(12) United States Patent
Sokulin et al.

(10) Patent No.: US 12,714,400 B1
(45) Date of Patent: Aug. 25, 2026

(54) SYSTEM FOR CROSS-SECTIONAL DISPLAY FOR THREE- DIMENSIONAL ULTRASOUND IMAGING

(71) Applicant: GE Precision Healthcare LLC, Waukesha, WI (US)

(72) Inventors: Ella Sokulin, Kiryat Tivon (IL); Alexander Sokulin, Kiryat Tivon (IL); Doron Shaked, Kiryat Tivon (IL); Carmit Shiran, Middleton, WI (US); Roei Gelbhart, Tel-Aviv (IL); Menachem Halmann, Monona, WI (US); Or Elezra, Haifa (IL)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/171,061

(22) Filed: Apr. 4, 2025

(51) Int. Cl.
*A61B 8/00* (2006.01)
*A61B 8/08* (2006.01)

(52) U.S. Cl.
CPC .............. *A61B 8/483* (2013.01); *A61B 8/085* (2013.01); *A61B 8/466* (2013.01); *A61B 8/54* (2013.01)

(58) Field of Classification Search
CPC ......... A61B 8/483; A61B 8/085; A61B 8/466; A61B 8/54
See application file for complete search history.

(56) References Cited

U.S. PATENT DOCUMENTS

| | | | | |
|---|---|---|---|---|
| 10,667,793 | B2 | 6/2020 | Halmann et al. | |
| 2011/0060223 | A1 * | 3/2011 | Kim | G01S 7/52063 600/443 |
| 2016/0000408 | A1 * | 1/2016 | Matsunaga | A61B 8/463 600/443 |

(Continued)

FOREIGN PATENT DOCUMENTS

| | | |
|---|---|---|
| CN | 112819773 | 5/2021 |
| CN | 114820952 | 7/2022 |

(Continued)

OTHER PUBLICATIONS

Ramin Moshavegh et al., "Novel automatic detection of pleura and B-lines (comet-tail artifacts) on in vivo lung ultrasound scans," Proc. SPIE 9790, Medical Imaging 2016: Ultrasonic Imaging and Tomography, 97900K (Apr. 1, 2016) (Year: 2016).*

*Primary Examiner* — Chao Sheng
(74) *Attorney, Agent, or Firm* — Foley & Lardner LLP

(57) ABSTRACT

An ultrasound system includes a transducer configured to transmit and receive an ultrasound signal in a three-dimensional volume. The system includes a processing circuit having a processor and a memory device storing instructions that, when executed, cause the processing circuit to perform operations including identifying a first anatomical feature based on image data obtained from the three-dimensional volume where the first anatomical feature is along a cross-sectional plane, identifying at least one second anatomical feature based on the first image data, determining algorithm outputs including at least one of a number of second (Continued)

400
405 IDENTIFY A FIRST ANATOMICAL FEATURE
410 RECEIVE FIRST IMAGE DATA
415 IDENTIFY AT LEAST ONE SECOND ANATOMICAL FEATURE
420 DETERMINE ALGORITHM OUTPUTS
425 DISPLAY OUTPUT IMAGE BASED ON FIRST IMAGE DATA
430 DISPLAY OUTPUT IMAGE BASED ON ALGORITHM OUTPUTS anatomical features identified, an area of at least one of the second anatomical features, or an area of at least one of the second anatomical features divided by an area of the first anatomical feature, and displaying an output image based on at least one of the algorithm outputs or the first image data.

20 Claims, 18 Drawing Sheets

(56) References Cited

U.S. PATENT DOCUMENTS

| | | | | |
|---|---|---|---|---|
| 2017/0086794 | A1* | 3/2017 | Halmann | A61B 8/0875 |
| 2019/0105013 | A1* | 4/2019 | Wang | A61B 8/463 |
| 2020/0352547 | A1 | 11/2020 | Raju et al. | |
| 2022/0386998 | A1 | 12/2022 | Mehanian et al. | |
| 2024/0249498 | A1 | 7/2024 | Galeotti et al. | |

FOREIGN PATENT DOCUMENTS

| | | |
|---|---|---|
| IT | 201900006969 | 11/2020 |
| WO | WO-2014/195742 | 12/2014 |
| WO | WO-2021/003711 | 1/2021 |

* cited by examiner

700c

700d

800c

800d

SYSTEM FOR CROSS-SECTIONAL DISPLAY FOR THREE- DIMENSIONAL ULTRASOUND IMAGING

STATEMENT REGARDING FEDERALLY SPONSORED RESEARCH AND DEVELOPMENT

This invention was made with government support under Grant No. 75A50123C00035 awarded by Biomedical Advanced Research and Development Authority (BARDA). The Government has certain rights in the invention.

FIELD

Embodiments of the subject matter disclosed herein relate to ultrasound imaging, and more particularly, to the use of three-dimensional ultrasound imaging for cross-sectional display for detection of an anatomical feature.

BACKGROUND

During an ultrasound scan of a lung, an ultrasound probe is placed in a first orientation (e.g., a sagittal orientation towards a patient's head) by a technician, such as a sonographer. Identifying a number of B-lines is a challenge during the scan and the technician may move the ultrasound probe from the first orientation to a second orientation to capture a better scan of the B-lines, which can vary dependent on time, angle of the probe, and location. Images obtained during the ultrasound scan of B-lines may lead to missing B-lines or counting a B-line twice, leading to false or missed diagnosis if images are not optimal.

SUMMARY

An embodiment relates to an ultrasound imaging system. The ultrasound imaging system includes a transducer configured to transmit and receive an ultrasound signal in a three-dimensional volume. The three-dimensional volume includes a plurality of planes including a cross-sectional plane. The ultrasound imaging system also includes a processing circuit. The processing circuit includes a processor coupled to a memory device storing instructions thereon that, when executed, cause the processing circuit to perform operations including identifying a first anatomical feature based on initial image data obtained from the three-dimensional volume by an ultrasound probe along first planes intersecting a surface of the ultrasound probe, the first anatomical feature determined to be along the cross-sectional plane, receiving at least one first image data from the three-dimensional volume parallel to the cross-sectional plane, identifying at least one of a second anatomical feature based on the at least one first image data, determining algorithm outputs based on the at least one first image data. The algorithm outputs include at least one of a number of the second anatomical feature identified, an area of the second anatomical feature, or an area of the second anatomical feature divided by an area of the first anatomical feature. The operations include displaying at least one of the algorithm outputs or an output image based on the first image data on a display screen of the ultrasound imaging system.

Another embodiment relates to an ultrasound imaging system. The ultrasound imaging system includes a transducer configured to transmit and receive an ultrasound signal in a three-dimensional volume. The three-dimensional volume includes a plurality of planes including a cross-sectional plane. The ultrasound imaging system includes an image processing circuit configured to identify a first anatomical feature based on initial image data and receive first image data from the three-dimensional volume parallel to the cross-sectional plane. The ultrasound imaging system includes a control circuit configured to determine algorithm outputs based on the first image data. The algorithm outputs include at least one of a number of second anatomical features identified, an area of at least one of the second anatomical features, or an area of at least one of the second anatomical features divided by an area of the first anatomical feature. The ultrasound imaging system is configured to display an output image based on at least one of the algorithm outputs or the first image data on a display screen of the ultrasound imaging system.

Another embodiment relates to a method. The method includes identifying, by a processing circuit, a first anatomical feature based on initial image data obtained from a three-dimensional volume by an ultrasound probe along first planes intersecting a surface of the ultrasound probe. The first anatomical feature determined to be along a cross-sectional plane. The method includes receiving, by the processing circuit, first image data from the three-dimensional volume parallel to the cross-sectional plane. The method includes identifying, by the processing circuit, at least one second anatomical feature based on the first image data. The method includes determining, by the processing circuit based on the first image data, algorithm outputs including at least one of a number of second anatomical features identified, an area of at least one of the second anatomical features, or an area of at least one of the second anatomical features divided by an area of the first anatomical feature. The method includes displaying an output image based on at least one of the algorithm outputs or the first image data on a display screen of an ultrasound imaging system.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
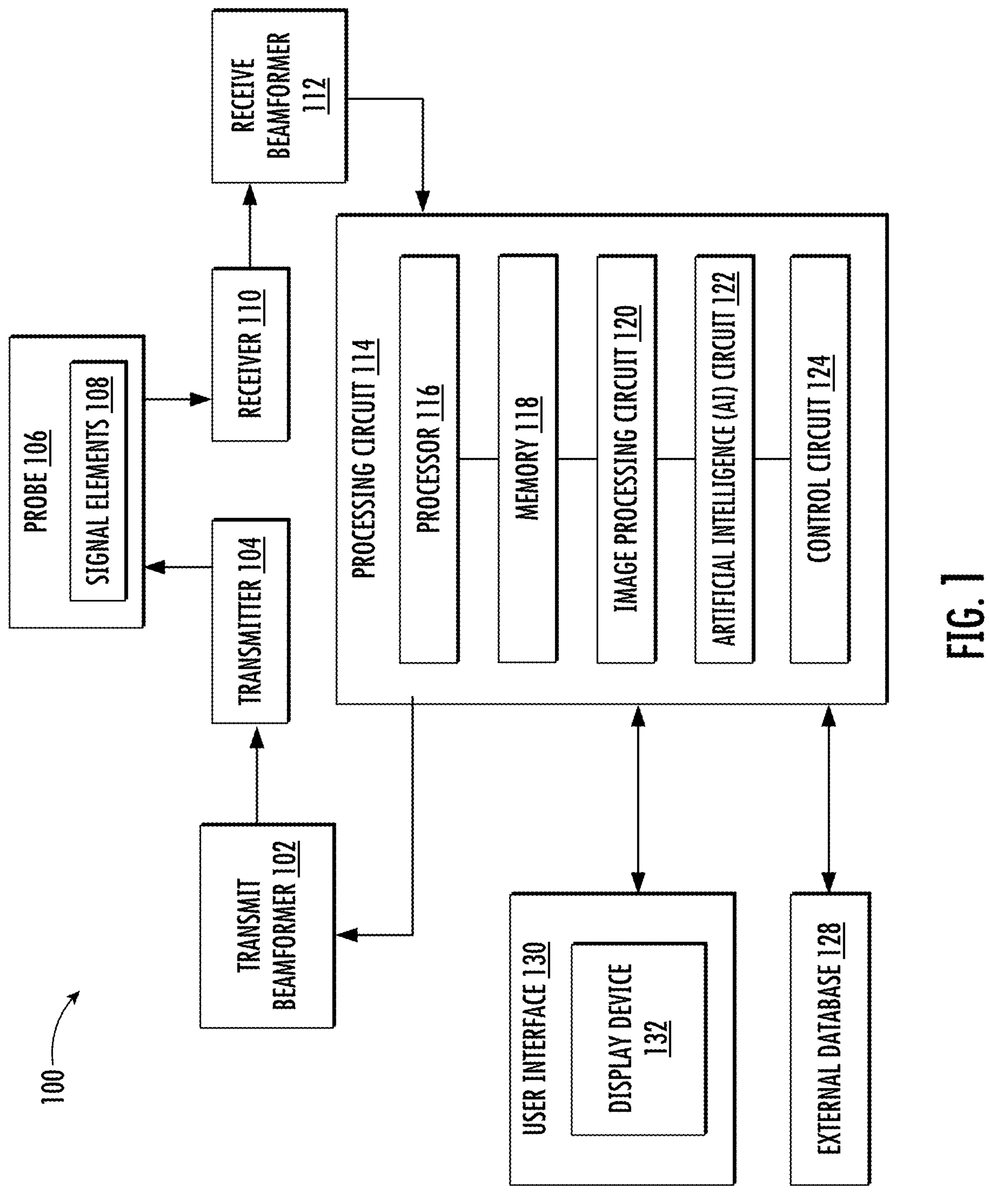
FIG. 1 is a block diagram of an ultrasound imaging system, according to an example embodiment.

Referring generally to the figures, systems and methods for the use of three-dimensional ultrasound imaging for cross-sectional plane display to detect an anatomical feature are disclosed. The systems disclosed herein are used to obtain a plurality of image data along cross-sectional planes. The system disclosed herein use the plurality of images to identify at least one of an anatomical feature. The systems and methods use the plurality of images such that a user interface may display an image based on first image data or based on second image data obtained from determining a plane perpendicular to the cross-sectional plane in which the anatomical feature appears.

During an ultrasound scan of a lung, an ultrasound probe is conventionally positioned in a sagittal orientation (e.g., pointed towards a patient's head). Generally, however, identifying a number and volume of B-lines present between a pair of ribs is challenging and an acquired image at the orientation may not be of sufficient quality to adequately identify all B-lines or to make a proper diagnosis. Visualization of B-lines is important for evaluating the lung and searching for pathologies around the pleura. For example, more than three B-lines present may indicate a medical condition (e.g., pulmonary edema). The lack of quality in the image may be due to artifacts, a lack of visualization of the pleura, and probe orientation. Thus, it is desired to orient the probe such that a resultant image data from an ultrasound beam from the probe captures a consistent number of B-lines. At such an orientation, the pleura is at an optimal view and the B-lines can be clearly seen. Manually orienting the ultrasound probe without assistance such that the resultant image data captures a consistent number of B-lines is time consuming and relies on the skills and expertise of the operator (e.g., sonographer, technician, clinician, etc.), thereby resulting in inconsistencies due to operator efficiencies and in obtaining consistent and high-quality ultrasound images.

Consistency in detecting the number of B-lines is important for proper diagnosis and treatment of a patient. For example, when treating a patient for a medical condition that is related to the number of B-lines (e.g., pulmonary edema), it is important to visualize the B-lines to ensure the number of B-lines are decreasing. However, if a consistent number of B-lines cannot be captured due to a number of reasons such as the skills or expertise of the operator, it may be difficult to properly ensure the B-lines are being accurately detected. For example, some B-lines might be missed in the captured image or B-lines might be counted twice in such situations.

The systems and methods described herein provide a technical solution to existing ultrasound imaging systems employ three-dimensional ultrasound imaging. The use of three-dimensional ultrasound imaging allows for a cross-sectional plane (e.g., substantially parallel to a patient's skin, a plane that does not intersect with a surface/footprint of the probe) to be obtained to visualize B-lines. The use of three-dimensional imaging allows for the cross-sectional plane to be obtained. This differs from two-dimensional imaging, in which only slices that extend into a body can be obtained. Defining a Cartesian coordinate system as an XYZ coordinate system, in which Z is an axis that extends into a patient's body, two-dimensional ultrasound imaging obtains scans from either an XZ plane or a YZ plane. In other words, scans are obtained from planes that extend into the body, as shown with reference to FIGS. 5A and 5B, among others. With three-dimensional imaging, images from the XY plane (i.e., the cross-sectional plane) may be obtained. As described herein, the XY plane may provide more information on anatomical features, such as the B-lines.

Using the cross-sectional plane, a number of B-lines and an area of the B-lines can be determined. Furthermore, as the B-lines move with the pleura, using the pleura to determine the cross-sectional plane may be performed by the system. The cross-sectional plane may then be used to determine a plane perpendicular to the cross-sectional plane (e.g., a plane that includes depth) in which the B-lines appear. The systems and methods described herein can be used to generate a visualization of a number of anatomical features, such as B-lines and Z-lines, among others.

Thus, the systems and methods described herein reduce the dependency on the expertise and skills of the operator by automatically determining a plane in which an anatomical feature appears through the use of cross-sectional planes. Additionally, the system may use a second anatomical feature to determine the cross-sectional planes, thereby reducing the need for the operator to maneuver the probe manually to reach that view. Furthermore, the systems and methods described herein assist an operator in detecting a pathology and completing an ultrasound exam in a shorter amount of time (e.g., due to the operator not having to manually adjust the probe to obtain the desired orientation in which the anatomical feature appears).

The implementations described herein address a technical problem by providing enhanced data integration and analysis capabilities, which deliver a particular technical solution that streamlines and refines generating images during a lung ultrasound. The systems described herein are implemented to improve how data is synthesized and utilized from various sources that provide information relating to an optimal orientation for capturing images during an ultrasound scan. By assessing specific anatomical features and automatically determining cross-sectional images and anatomical features based on the assessment, these systems provide real-time guidance for detecting anatomical features to generate images during an ultrasound scan. Accordingly, the approaches disclosed herein provide a specific technical improvement to various technical problems, including those set forth herein. The systems described herein may also reduce processing power by performing various processing operations simultaneously to generate images during an ultrasound scan, rather than performing a plurality of processing operations individually and consuming unnecessary processing power.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring to FIG. 1, a schematic diagram of an ultrasound imaging system 100 is shown. The ultrasound imaging system 100 may be used in a medical environment (e.g., hospitals, clinics, etc.), for example, by a sonographer, technician, or other clinician certified to collect ultrasound data from a patient.

An example of a procedure performed using the ultrasound imaging system 100 may be a lung ultrasound. The lung ultrasound may be performed to detect various pulmonary pathologies such as pneumonia, pulmonary edema, pleural effusion, pneumothorax (e.g., a collapsed lung), pulmonary embolism, lung cancer, and so on. Such pathologies are detected by collecting and processing ultrasound data (e.g., using the ultrasound imaging system 100, as described herein). During the lung ultrasound, a sonographer collects the ultrasound data by navigating a probe (e.g., probe 106, as described below) over a patient's chest until a sufficient volume of ultrasound images are collected. With three-dimensional imaging, using the ultrasound imaging system 100, a three-dimension volume of ultrasound images may be obtained. The sonographer may collect the ultrasound images both with the ultrasound probe in a sagittal orientation, a transverse orientation, and a coronal orientation. With reference to the Cartesian coordinate system described herein, the transverse orientation refers to the XZ plane or the YZ plane. The sagittal orientation refers to the other of the XZ plane or the YZ plane. The coronal orientation refers to the XY plane. As described herein, the coronal orientation may be particularly beneficial in instances where a pulmonary pathology is detected. The collected images are stored in a central storage device (e.g., memory 118) and analyzed by the sonographer. The sonographer generates a set of measurements from the images (e.g., 50-100 records), and the images and measurements are collectively reviewed by a medical expert, such as a pulmonologist. The pulmonologist provides any clinical findings/conclusions in a report submitted to the patient's medical record.

As shown in FIG. 1, the ultrasound imaging system 100 includes a transmit beamformer 102, a transmitter 104, a probe 106, a receiver 110, and a receive beamformer 112. The ultrasound imaging system 100 may also include a matching layer and a damping block. The matching layer improves ultrasound image quality by having an acoustic impedance between a tissue to be imaged and a material of a transducer of the ultrasound imaging system 100. The damping block is configured to absorb ultrasound energy to improve ultrasound image quality.

The transmit beamformer 102 may be either a hardware beamformer or a software beamformer. In embodiments where the transmit beamformer 102 is a hardware beamformer, the transmit beamformer 102 may include one or more of a graphics processing unit (GPU), a microprocessor, a central processing unit (CPU), a digital signal processor (DSP), or any other type of processor capable of performing logical operations. The transmit beamformer 102 may be configured to perform conventional beamforming techniques as well as techniques such as retrospective transmit beamforming (RTB). Alternatively, in embodiments where the transmit beamformer 102 is a software beamformer, a processor (e.g., processor 116, as described below) may be configured to perform some or all of the functions associated with the transmit beamformer 102.

The probe 106 may be a linear array probe, a curvilinear array probe, a sector probe, a row-column array probe, or any other type of probe configured to obtain ultrasound data (e.g., B-mode data, color flow data, etc.). More specifically, the probe 106 may be any type of probe including a matrix transducer array (e.g., matrix configuration 300, as described below with reference to FIG. 3) configured to obtain three-dimensional (3D) ultrasound data. In some embodiments, the probe 106 may include a position sensor configured to detect a position of the probe 106 relative to one or more reference locations. That is, the position sensor may continuously track movement (e.g., rotation, translation, orientation, etc.) of the probe 106 relative to the location of the probe 106 when the anatomy being imaged is identified. For example, the anatomy being imaged may be identified as a pleura (e.g., represented by pleura 502, as described below) at a first location of the probe 106. Then, the position sensor may track the movement of the probe 106 relative to the pleura to identify successive locations of the probe 106. In some embodiments, the position sensor may transmit position data to be stored within the ultrasound imaging system 100 (e.g., in memory 118).

The probe 106 may include a transducer configured to transmit and receive an ultrasound signal. In some embodiments, as shown in FIG. 1, the probe 106 includes signal elements 108. The signal elements 108 may be arranged in a transducer array, and in some embodiments may be arranged in a 2D array (e.g., as illustrated by the matrix configuration 300 shown in FIG. 3). As described herein, the 2D array of the signal elements 108 may allow for 3D ultrasound imaging (e.g., such that the transducer is configured to transmit and receive a 3D ultrasound signal). The transmit beamformer 102 and the transmitter 104 drive the signal elements 108 to emit pulsed ultrasonic signals into a body of a subject (e.g., a patient). For example, during a lung ultrasound, a sonographer or other clinician may navigate the probe 106 over a patient's chest so that the signal elements 108 in the probe 106 emit the pulsed ultrasonic signals into the patient's thoracic cavity. The pulsed ultrasonic signals are then back-scattered from anatomical structures in the body, such as blood cells or muscular tissues, to produce echoes that return to the signal elements 108. During a lung ultrasound, however, there is a mismatch in the acoustic impedance between the lung (e.g., due to the lung being full of air) and the material of the transducer, meaning the ultrasonic signals are unable to back-scatter from the air-filled lung. Rather, the ultrasonic signals back-scatter from the pleura (e.g., causing generation of the pleura 502 in an ultrasound image of the lung, as described below with reference to FIG. 5).

Additionally, in ultrasound imaging systems with electronically steered beams, the transmit beamformer 102 may be adjusted to shift an angle of the ultrasound beam, therefore shifting the ultrasound signal transmitted. For example, the transmit beamformer 102 may adjust timing and phase shifts of the ultrasound signals sent into the body of the subject to change the angle of the ultrasound signal. In various embodiments, the adjustment may occur without the operator having to move the transducer.

The receiver 110 receives the echoes from the probe 106 and converts the echoes into electrical signals. The electrical signals are then passed through the receive beamformer 112, which produces the ultrasound data from the electrical signals. As described above with reference to the transmit beamformer 102, the receive beamformer 112 may be either a hardware beamformer or a software beamformer. In embodiments where the receive beamformer 112 is a hardware beamformer, the receive beamformer 112 may include one or more of a GPU, a microprocessor, a CPU, a DSP, or any other type of processor capable of performing logical operations. The receive beamformer 112 may be configured to perform conventional beamforming techniques as well as techniques such as retrospective transmit beamforming (RTB). Alternatively, in embodiments where the receive beamformer 112 is a software beamformer, a processor (e.g., processor 116, as described below) may be configured to perform some or all of the functions associated with the receive beamformer 112.

Although the transmit beamformer 102, the transmitter 104, the receiver 110, and the receive beamformer 112 are shown in FIG. 1 as being components of the ultrasound imaging system 100 that are distinct from the probe 106, it should be appreciated that in some embodiments, the probe 106 may include electronic circuitry configured to perform the functions of each of the transmit beamformer 102, the transmitter 104, the receiver 110, and/or the receive beamformer 112. That is, all or part of the transmit beamformer 102, the transmitter 104, the receiver 110, and/or the receive beamformer 112 may be situated within the probe 106.

Referring still to FIG. 1, the ultrasound imaging system 100 is shown to include a processing circuit 114. As shown, the processing circuit 114 may include at least one processor 116, a memory 118, an image processing circuit 120, an artificial intelligence (AI) circuit 122, and a control circuit 124. In this way, the processing circuit 114 may be structured or configured to execute or implement the instructions, commands, and/or control processes described herein with respect to the processor 116, the memory 118, the image processing circuit 120, the AI circuit 122, and the control circuit 124. While shown as being separate from the probe 106 in FIG. 1, it will be appreciated that the processing circuit 114 can be part of the probe 106. For example, the processing circuit 114 can be disposed in a handheld housing of the probe 106 (e.g., in the case of the probe 106 being a wireless probe).

The processor 116 may include a CPU, a GPU, a microprocessor, a DSP, a general-purpose single- or multi-chip processor, a field-programmable gate array (FPGA), or any other type of processor capable of performing logical operations. A general-purpose processor may be a microprocessor, or, any conventional processor, or state machine. A processor also may be implemented as a combination of computing devices, such as a combination of a DSP and a microprocessor, a plurality of microprocessors, one or more microprocessors in conjunction with a DSP core, or any other such configuration. In some embodiments, the processor 116 may be shared by multiple circuits (e.g., the circuits of the processor 116 may include or otherwise share the same processor which, in some example embodiments, may execute instructions stored, or otherwise accessed, via different areas of the memory 118). Alternatively or additionally, the processor 116 may be structured to perform or otherwise execute certain operations independent of one or more co-processors. In some embodiments, two or more processors may be coupled via a bus to enable independent, parallel, pipelined, or multi-threaded instruction execution. All such variations are intended to fall within the scope of the present disclosure.

The processor 116 may be configured to control the transmit beamformer 102, the transmitter 104, the receiver 110, and the receive beamformer 112. The processor 116 may also be in electronic communication with the probe 106. For purposes of this disclosure, the term "electronic communication" may be defined to include both wired and wireless communications.

In some embodiments, the processor 116 may be configured to control the probe 106 during data acquisition. That is, the processor 116 may control the data acquisition by controlling which of the signal elements 108 are active and by controlling a shape of the beam emitted from the probe 106. For example, using the matrix configuration 300 of the signal elements 108 shown in FIG. 3, the processor 116 may be configured to control a transmit direction of the probe 106 such that data is acquired from a sagittal plane (e.g., azimuthal plane 210) and/or a transverse plane (e.g., elevation plane 215) of the probe 106. According to other embodiments, the transmit direction of the probe 106 may be controlled by another component of the ultrasound imaging system 100 (e.g., the control circuit 124).

Alternatively or additionally, the processor 116 may include a complex demodulator configured to demodulate radio frequency (RF) data obtained by the probe 106 and generate raw data. According to other embodiments, the demodulation of the RF data may be performed by another component of the ultrasound imaging system 100. The processor 116 may perform the processing operations described herein according to a plurality of selectable ultrasound modalities.

Depending on a mode of operation of the ultrasound imaging system 100, the processor 116 may process ultrasound data obtained by the probe 106 according to the mode of operation to generate image data. For example, the mode of operation may include B-mode, color flow Doppler mode, M-mode, color M-mode, spectral Doppler, elastography, TVI, strain, strain rate, and the like. Various of these modes of operation may be configured to, for instance, convert ultrasound data from beam space coordinates (e.g., received from the receive beamformer 112) to display space coordinates (e.g., such that the ultrasound data may be displayed as image data). In some embodiments, the mode of operation may allow for video processing by the processor 116 such that a series of images (e.g., processed ultrasound data) may be displayed in real-time while a scanning session/procedure is being performed on a patient. An operator of the ultrasound imaging system 100 (e.g., a sonographer) may switch between various modes to obtain a variety of ultrasound data and to perform a complete scan of an anatomical region of interest. For example, the operator may switch between modes using user interface 130 (e.g., using physical controls, interface inputs representing physical controls, etc.).

The processor 116 performs the processing operations in real-time as the echo signals are received by the receiver 110 from the probe 106. For the purposes of this disclosure, the term "real-time" is defined to include a procedure that is performed without any intentional delay. As an illustrative, non-limiting example, in certain instances, the ultrasound imaging system 100 may obtain images at a real-time volume-rate of 7-20 volumes/sec. It should be appreciated, however, that the real-time volume-rate may be dependent on the length of time that it takes to obtain each volume of data for display. Thus, the ultrasound imaging system 100 may be configured to obtain 2D data of an anatomical region at a faster rate than 3D data of the same anatomical region because it takes longer to obtain a volume of 3D data than the same volume of 2D data. Similarly, when the ultrasound imaging system 100 obtains a relatively large volume of data, the real-time volume-rate may be slower than for a smaller volume of data. For example, during an abdominal scan, the real-time volume-rate may be slower if the patient is an adult versus if the patient is an infant because the volume of data is larger for the adult than for the infant (e.g., due to the abdomen of an adult being larger than the abdomen of an infant). Therefore, certain implementations of the ultrasound imaging system 100 may have real-time volume-rates that are faster than 20 volumes/sec, while other implementations of the ultrasound imaging system 100 may have real-time volume-rates that are slower than 7 volumes/sec.

In some embodiments, the ultrasound imaging system 100 may include multiple processors configured to perform the processing operations/functionality described with reference to processor 116. For example, in such embodiments, a first processor of the multiple processors may be configured to demodulate and decimate the RF signal while a second processor of the multiple processors may be configured to further process the RF data prior to displaying an image representative of the data. It should be appreciated that other embodiments may use a different arrangement of processors.

The processor 116 may also be in electronic communication with the display device 132 such that the processor 116 may process ultrasound data obtained by the probe 106 and generate images to display on the display device 132 (e.g., first ultrasound image 500*a*, second ultrasound image 500*b*, first ultrasound image 700*a*, and second ultrasound image 700*b* as described below with reference to FIGS. 5A, 5B, 7A, and 7B).

As shown in FIG. 1, the processing circuit 114 also includes the memory 118. The memory 118 may be configured to, for example, store processed volumes of data obtained by the ultrasound imaging system 100 (e.g., ultrasound data collected by the probe 106). For example, the memory 118 may be a hospital picture archiving and communication system (PACS). The memory 118 (e.g., memory, memory unit, storage device, etc.) may include one or more devices (e.g., RAM, ROM, Flash memory, hard disk storage, etc.) for storing data and/or computer code for completing or facilitating the processes, layers, and modules described in the present application. The memory 118 may be or include tangible, non-transient volatile memory or non-volatile memory. The memory 118 may also include database components, object code components, script components, or any other type of information structure for supporting the activities and information structures described in the present application.

In various embodiments, the memory 118 may have varying capacity (e.g., storage space) across embodiments of the ultrasound imaging system 100. For example, the memory 118 may be configured to store at least 60 minutes' worth of ultrasound data. The ultrasound data may be stored in the memory 118 such that the ultrasound data may be retrieved according to an order/time of acquiring the data. That is, the ultrasound data may be stored with a timestamp indicating a time at which the ultrasound data was collected and may be retrieved starting with an oldest time at which the ultrasound data was collected.

The processing circuit 114 also includes the image processing circuit 120, the AI circuit 122, and the control circuit 124. Each of the image processing circuit 120, the AI circuit 122, and the control circuit 124 are configured to facilitate determination of the second transmit direction using the probe 106 during an ultrasound scan.

The image processing circuit 120 is configured to analyze ultrasound image data (e.g., obtained using the probe 106, stored in the memory 118, etc.) and identify anatomical structures, scanning planes, transmit directions, pathologies, and/or other features depicted by/contained within the image data. In some instances, the image processing circuit 120 may include multiple deep learning-based models configured to analyze the image data. Alternatively or additionally, the image processing circuit 120 may use multiple deep learning-based models included in the AI circuit 122 to analyze the image data, as described herein.

Figure 8A:
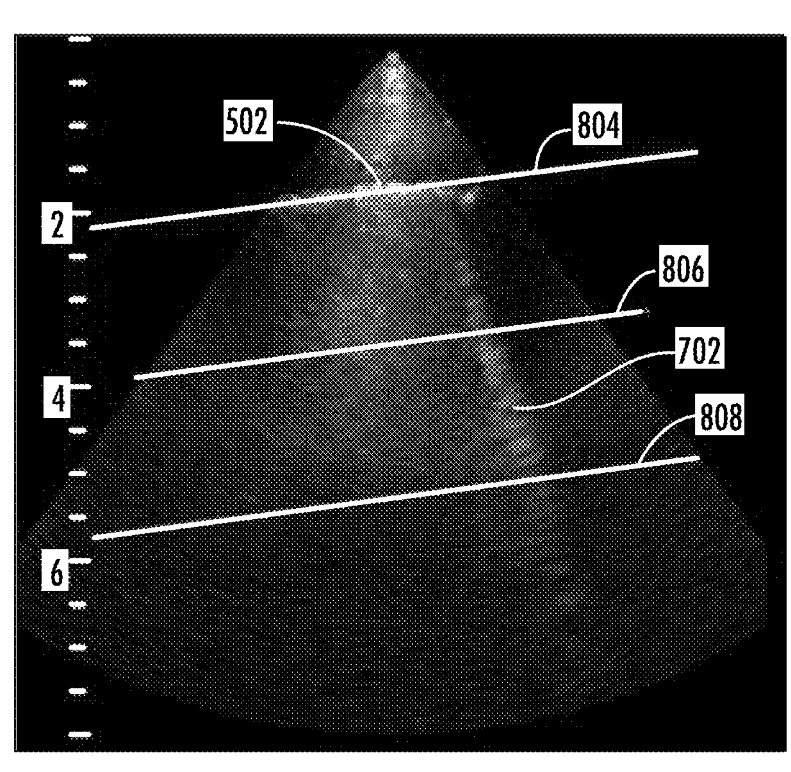
FIG. 8A is an illustration of another ultrasound image acquired from the three-dimensional volume using an ultrasound probe, according to an example embodiment.
Figure 8B:
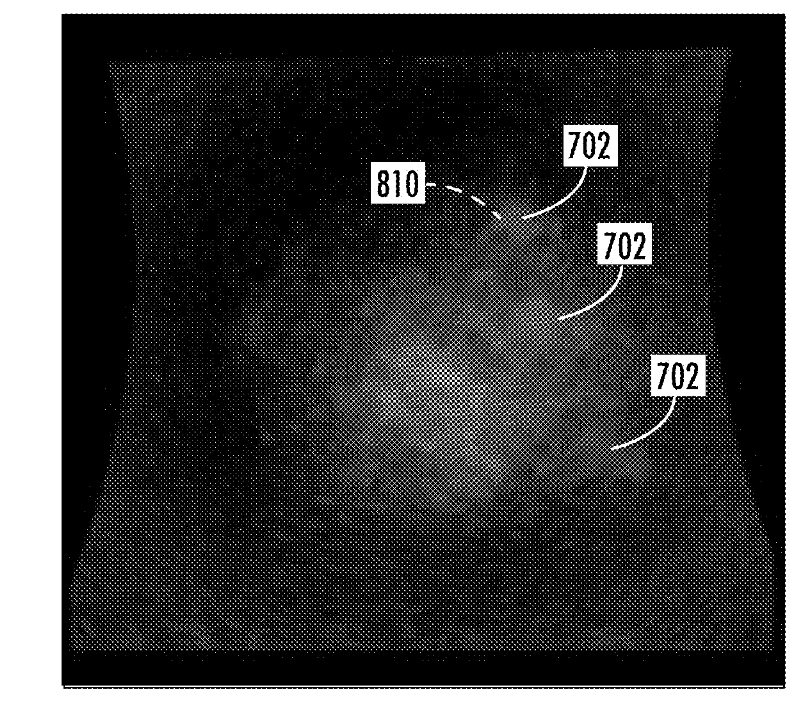
FIG. 8B is an illustration of another ultrasound image acquired from a first cross-sectional plane of the ultrasound image of FIG. 8A, according to an example embodiment.
Figure 8C:
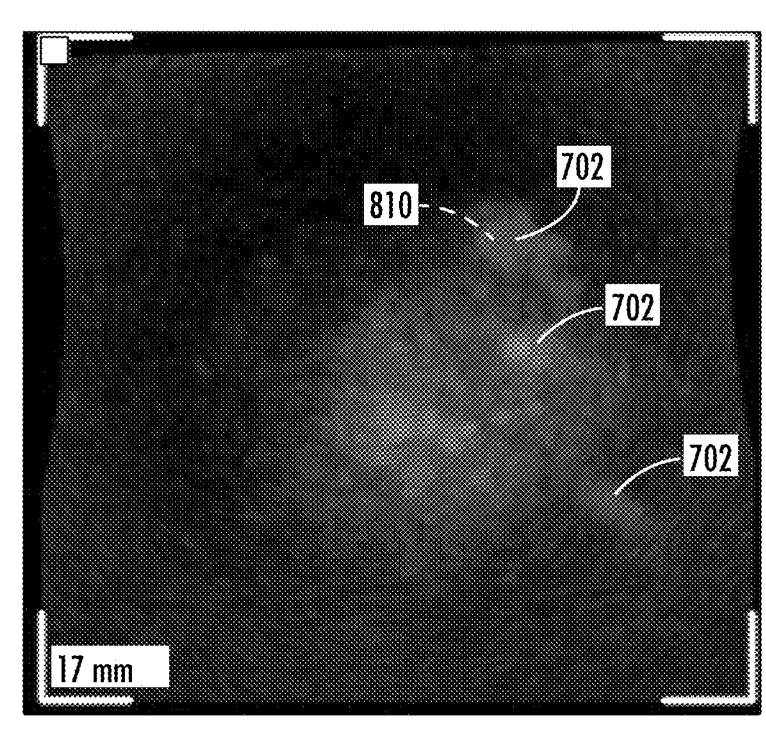
FIG. 8C is an illustration of another ultrasound image acquired from a second cross-sectional plane of the ultrasound image of FIG. 8A, according to an example embodiment.
Figure 8D:
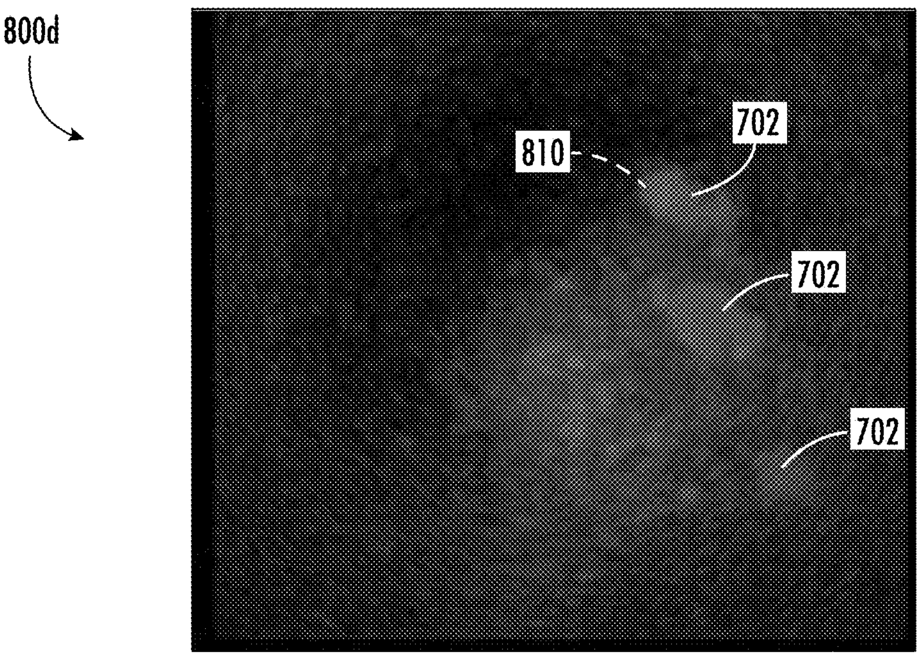
FIG. 8D is an illustration of another ultrasound image acquired from a third cross-sectional plane of the ultrasound image of FIG. 8A, according to an example embodiment.
Figure 9A:
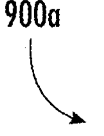
FIG. 9A is an illustration of another ultrasound image acquired from the three-dimensional volume using an ultrasound probe, according to an example embodiment.
Figure 9A:
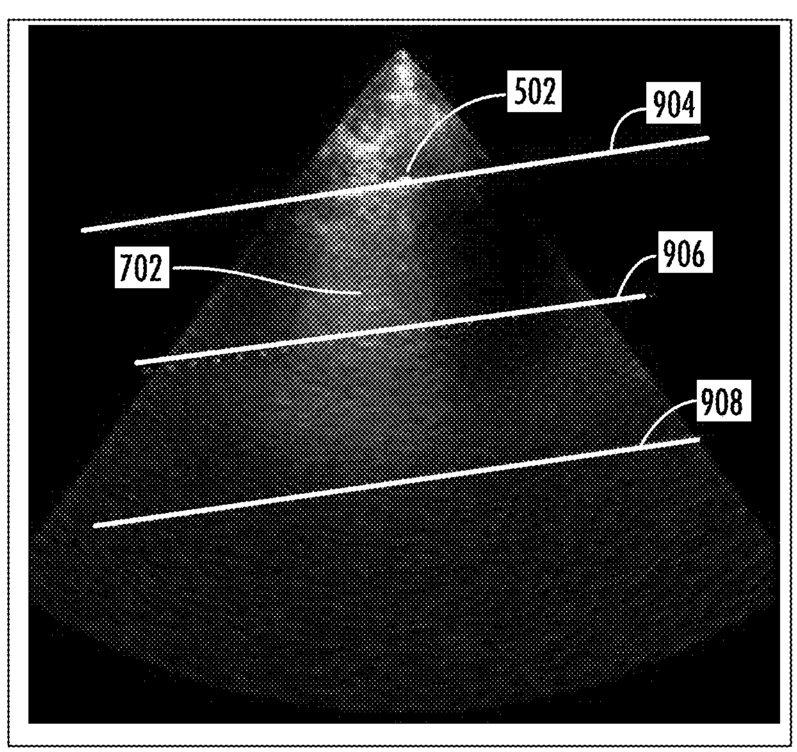
Figure 9B:
FIG. 9B is an illustration of another ultrasound image acquired from a first cross-sectional plane of the ultrasound image of FIG. 9A, according to an example embodiment.
Figure 9B:
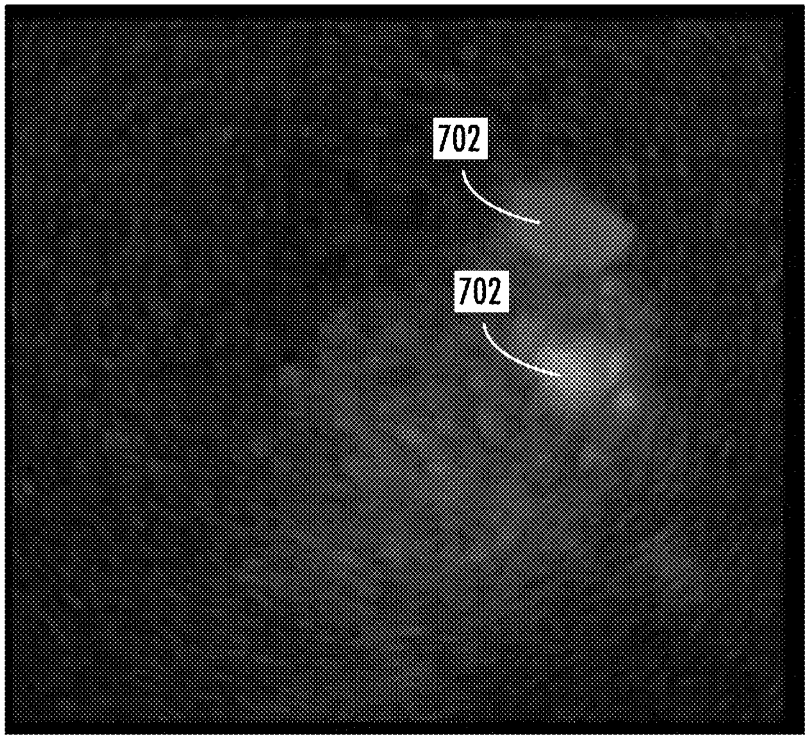
Figure 9C:
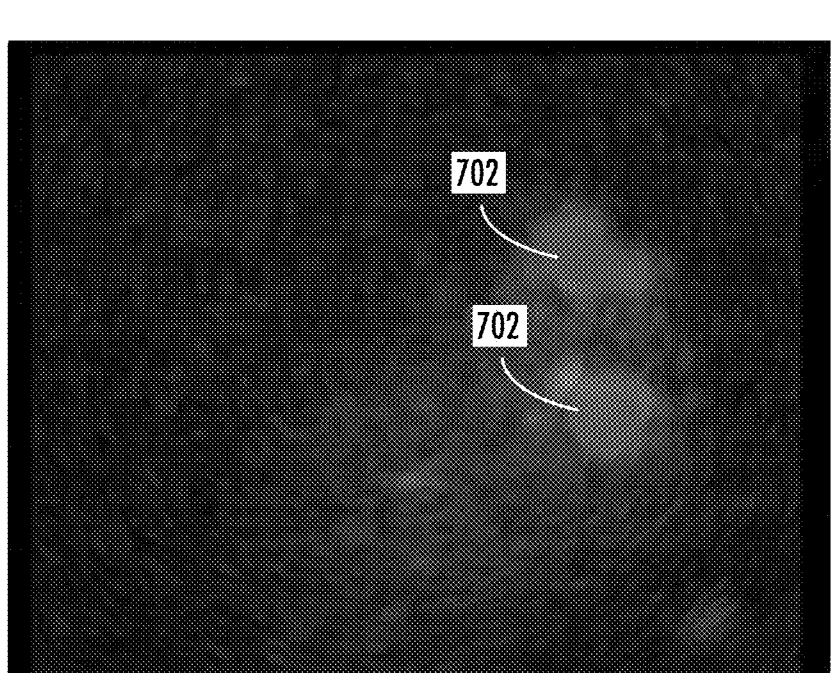
FIG. 9C is an illustration of another ultrasound image acquired from a second cross-sectional plane of the ultrasound image of FIG. 9A, according to an example embodiment.
Figure 9D:
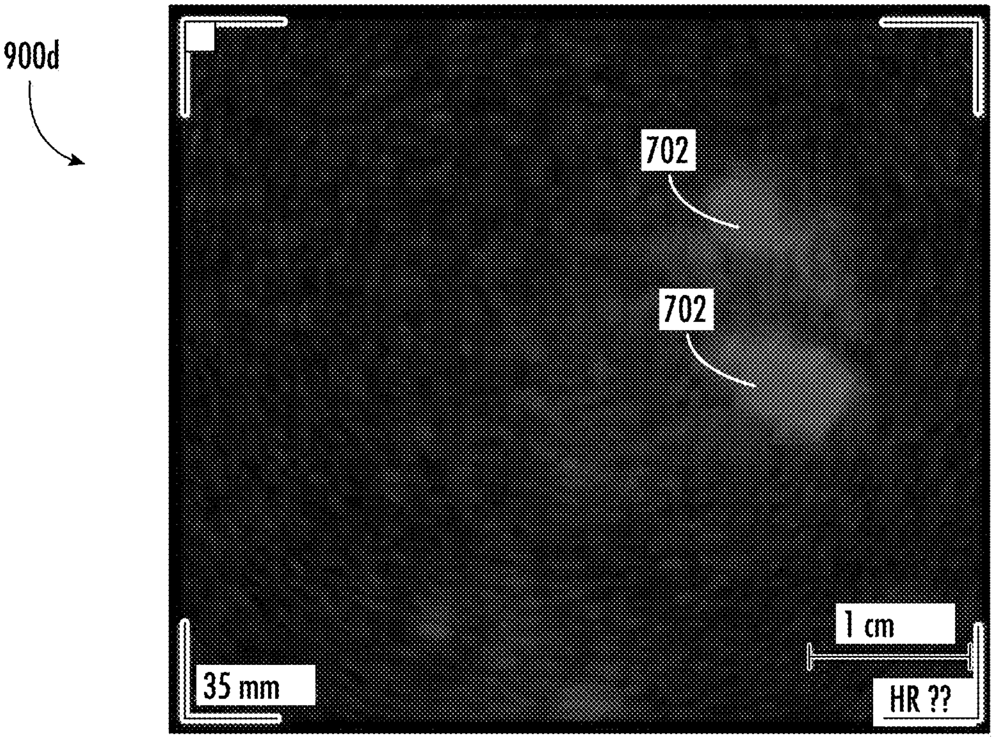
FIG. 9D is an illustration of another ultrasound image acquired from a third cross-sectional plane of the ultrasound image of FIG. 9A, according to an example embodiment.

In some embodiments, the image processing circuit 120 may be configured to identify an anatomical structure, feature, region, etc. captured by the image data. For example, during a lung ultrasound, the image processing circuit 120 may be configured to identify B-lines, Z-lines, the pleura, rib bones, shadows of the rib bones, and/or other pulmonary structures/features/regions depicted in the image data. The image processing circuit 120 may be configured to identify the anatomical structure using one or more algorithms (e.g., image processing algorithms such as edge detection, machine learning models, deep neural networks, etc.). In some embodiments, the image processing circuit 120 may be configured to apply one or more algorithms used by the AI circuit 122 and/or retrieved from the external database 128. For example, as described below with reference to FIGS. 7A and 7B, the image processing circuit 120 may use one or more algorithms to assess the pleura 502 (e.g., using a segmentation model to segment the pleura 502, using linear regression to estimate pleural lines) captured by the image data. In this way, the image processing circuit 120 may be configured to estimate a location and/or a plane of the pleura 502, and the transmit direction of the probe 106 may be adjusted based on the estimated direction with respect to an ultrasound beam such that the pleura can be scanned at a desired angle (e.g., at an angle where the pleura is perpendicular to the ultrasound beam), as described herein. The ultrasound beam refers to the transmitted ultrasound signal. In another example, as described below with reference to FIGS. 8B-8D, among others, the image processing circuit 120 may use one or more algorithms to assess the B-lines 702 captured by the image data. In this way, the image processing circuit may be configured to determine the B-lines 702 with an AI model, among other models.

In some embodiments, the image processing circuit 120 may identify anatomical features such as bones, blood vessels, organs, etc., based on a shape, relative proximity, apparent depth, orientation, etc. of said features in the image data. Then, based on the identified anatomical features, the image processing circuit 120 may be configured to determine the anatomical structure depicted in the image data. For example, because a lung is not able to be imaged directly (e.g., due to the lung being full of air and the mismatch in the acoustic impedance between the air and the transducer of the probe 106), the image processing circuit 120 may determine that the lung is being imaged based on a movement and/or orientation of the lung relative to surrounding structures, such as the pleura, via a deep learning classification model trained to recognize the movement and/or orientation of the lung, and other anatomical structures. In some embodiments, the image processing circuit 120 may detect movement of structures in the image data by comparing the location, shape, size, etc., of identified structures across a set of images (e.g., a cine loop).

According to some embodiments, the image processing circuit 120 may be configured to identify a view or a scanning plane from which the ultrasound data is obtained. For example, the image processing circuit 120 may be configured to identify whether the image data depicts a sagittal view (e.g., along azimuthal plane 210, XZ plane, YZ plane), a transverse view (e.g., along elevation plane 215, XZ plane, YZ plane), and/or a coronal view (e.g., parallel to a patient's body/skin, XY plane). Additionally, the image processing circuit 120 may be configured to identify a transmit direction from which the ultrasound data is obtained. For example, the image processing circuit 120 may be configured to use position data of the probe 106 to determine the transmit direction of the probe 106 with respect to an identified anatomical feature.

The image processing circuit 120 may also be configured to determine the presence of a pathology (e.g., an injury, disease, abnormality, etc.) in the image data. In some embodiments, the image processing circuit 120 may use a deep learning classification model trained to recognize various pathologies in the anatomical structure represented by the image data to specify the pathology that is present. Continuing with the example of the lung ultrasound, the image processing circuit 120 may use a deep learning classification model trained to recognize pulmonary pathologies to determine whether a pathology is present in the image data from the lung ultrasound. For instance, the image processing circuit 120 may identify pleural effusion (e.g., a buildup of fluid) in the pleura as a pulmonary pathology present in the image data. In some embodiments, the AI circuit 122 may be configured to perform any of the functions of the image processing circuit 120 described herein using multiple deep learning-based models configured to analyze the image data.

Based on the analysis of the image data, processing circuit 114 (e.g., the AI circuit 122) may be configured to determine an adjustment to the probe 106. In some embodiments, the adjustment to the probe 106 may include a change in the angle of the probe 106. For example, during a lung ultrasound, the image processing circuit 120 may determine an estimated angle of the pleura with respect to the ultrasound beam (e.g., using a plurality of images obtained from a sagittal plane, a coronal plane, and a transverse plane), and the processing circuit 114 may determine, a transmit direction to which the angle of the probe 106 is adjusted to (e.g., by adjusting the transmit beamformer 102). As another example, the control circuit 124 may determine a plane in which an anatomical feature lies in, as described below with reference to step 405 of method 400. As another example, the control circuit 124 may determine a plane perpendicular to the coronal plane in which a second anatomical feature appears in, as described below with reference to step 420 of method 400. In this way, the image captured of the second anatomical feature (e.g., the B-lines 702) may be improved due to images obtained from a cross-sectional plane by the probe 106 being analyzed to determine a plane (e.g., from the transverse and/or sagittal view) in which a number (e.g., a maximum number) of the second anatomical feature appears (e.g., such that detection is improved, as is shown in FIGS. 10C and 10D). The cross-sectional plane may be from the coronal view or may be any plane that does not intersect with a surface or footprint of the probe 106. For example, the cross-sectional plane may be from a plane that is parallel to the coronal view plus a deviation.

In some embodiments, the processing circuit 114 (e.g., the AI circuit 122) may be configured to automatically generate a control signal prompting an adjustment of the probe 106 based on the analysis of the image data performed by the image processing circuit 120. The control signal may be received by the control circuit 124, which may be configured to automatically align the transmit direction of the probe 106 such that the probe 106 is configured to acquire image data according to the transmit direction prescribed by the control signal. For example, the control signal may prompt the control circuit 124 to adjust the transmit beamformer 102, thereby adjusting the ultrasound beam, to shift the transmit direction of the probe 106.

The ultrasound imaging system 100 may also include an external database 128 and a user interface 130. The external database 128 refers to a database from which the processing circuit 114 (e.g., the image processing circuit 120, the AI circuit 122) retrieves information used in three-dimensional imaging during a lung ultrasound. For example, the external database 128 may be a medical information database. The medical information database may store clinical guidelines, standard practices, medical literature, medical textbooks, published research, previous case studies, and so on. Depending on an implementation of the ultrasound imaging system 100 and/or a procedure performed thereby, the processing circuit 114 may retrieve clinical guidelines, standard practices, medical literature, medical textbooks, published research, and previous case studies related to the implementation and/or procedure. For example, if the ultrasound imaging system 100 is being used in a hospital setting to conduct a lung ultrasound, the processing circuit 114 may retrieve clinical guidelines and standard practices related to the hospital setting and the lung ultrasound. Continuing with this example, the processing circuit 114 may also retrieve information from the medical literature, medical textbooks, published research, and previous case studies related to pulmonary anatomy and the lung ultrasound. In some instances, as described with reference to FIGS. 6A, 6B, and 8A-8D, among others, the information retrieved from the external database 128 may include one or more algorithms used to segment the anatomical feature and determine a plane that represents the anatomical feature (e.g., segmenting the pleura 502 and determining a plane using an algorithm).

The user interface 130 may be used by a sonographer or other clinician to control operation of the ultrasound imaging system 100. For example, the sonographer may use the user interface 130 to control the input of patient data, to change a scanning or display parameter, and/or to select various other modes, operations, parameters, etc. of the ultrasound imaging system 100. In some embodiments, the user interface 130 may include an off-the-shelf consumer electronic device such as a smartphone, a tablet, a laptop, and so on. For the purposes of this disclosure, the term "off-the-shelf consumer electronic device" is defined to be an electronic device that was designed and developed for general consumer use and one that was not specifically designed for use in a medical environment. Alternatively, in other embodiments, the user interface 130 may be an electronic device that was designed and developed for use in a medical environment.

According to some embodiments, the user interface 130 may be physically separate from the rest of the ultrasound imaging system 100 (e.g., the transmit beamformer 102, the transmitter 104, the probe 106, the receiver 110, the receive beamformer 112, the processing circuit 114, and/or the external database 128). The user interface 130 may communicate with the processor 116 through a wireless protocol, such as Wi-Fi, Bluetooth, wireless local area network (WLAN), near-field communication, and so on. According to some embodiments, the user interface 130 may communicate with the processor 116 through an application programming interface (API).

In some embodiments, the user interface 130 may include physical controls such as one or more of buttons, sliders, a rotary knob, a mouse, a keyboard, a trackball, hard keys linked to specific actions, soft keys that may be configured to control different functions, and so on. As shown in FIG. 1, the user interface 130 may also include a display device 132. In some embodiments, the display device 132 may be configured to display a graphical user interface (GUI) based on an instruction from the memory 118. The GUI may include user interface icons representing commands and instructions relating to the operation of the ultrasound imaging system 100. The user interface icons of the GUI may be configured such that a user (e.g., the sonographer, clinician, etc.) may select a specific user interface icon to initiate a specific function controlled by the GUI. For example, various user interface icons may be used to represent windows, menus, buttons, cursors, scroll bars, and so on. That is, the physical controls of the user interface 130 may be included as individual hardware elements, as user interface icons displayed on the display device 132, or as a combination of hardware elements and user interface icons.

In some embodiments, the display device 132 may include a touch-sensitive display device or a touch screen. According to such embodiments, the touch screen may be configured to interact with the GUI displayed by the display device 132 such that a user (e.g., the sonographer) can interact with the GUI via the touch screen. The touch screen may be a single-point touch screen that is configured to detect a single contact point at a time, or the touch screen may be a multi-point touch screen that is configured to detect multiple points of contact at a time. For embodiments where the touch screen is a multi-point touch screen, the touch screen may be configured to detect multi-point gestures involving contact from two or more of a user's fingers at a time. The touch screen may be a resistive touch screen, a capacitive touch screen, or any other type of touch screen that is configured to receive inputs from a stylus or one or more of a user's fingers. According to some embodiments, the touch screen may be an optical touch screen that uses technology such as infrared light or other frequencies of light to detect one or more points of contact initiated by a user. In some embodiments, the touch screen may be incorporated as part of the display device 132 or may be separate from the display device 132. The user interface 130 may also include a proximity sensor configured to detect objects and/or gestures that are within a predetermined distance (e.g., five feet, six inches, ten centimeters, etc.) of the proximity sensor. In various embodiments, the proximity sensor may be located on the display device 132 or as part of a touch screen that is separate from the display device 132.

Figure 2:
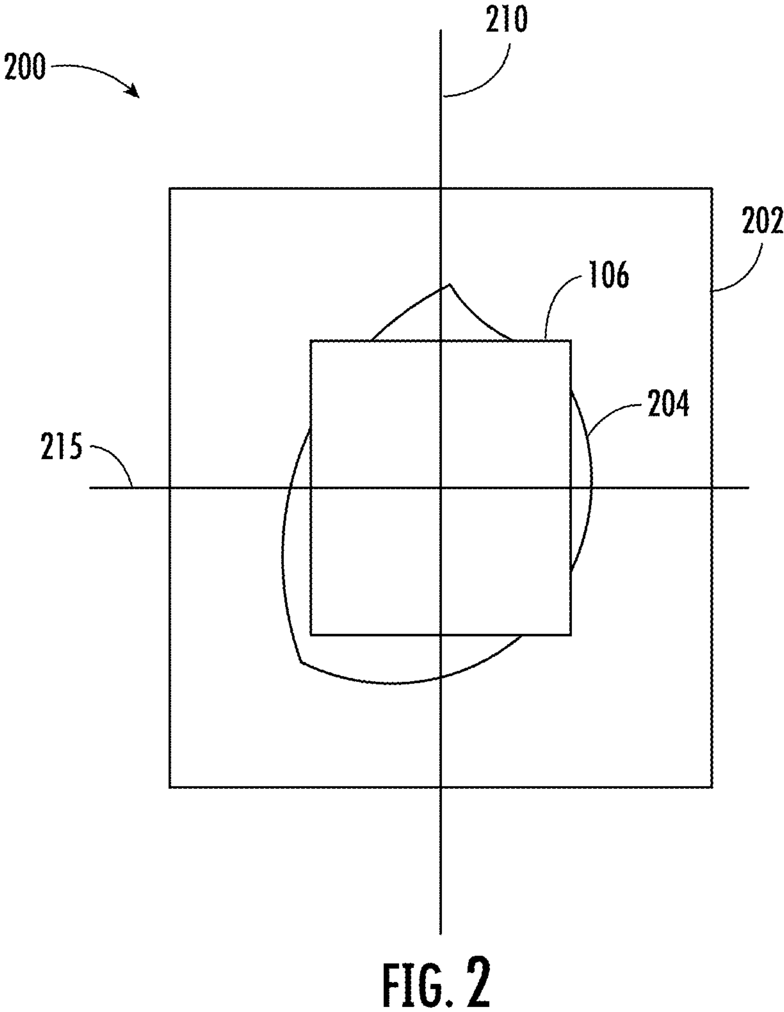
FIG. 2 is a diagram of a desired orientation of an ultrasound probe used in the ultrasound imaging system of FIG. 1, according to an example embodiment.

Referring to FIG. 2, an orientation 200 of the probe 106 is shown. The orientation 200 shown in FIG. 2 refers to a desired orientation of the probe 106 during a lung ultrasound, as described herein. More specifically, the orientation 200 refers to an orientation of the probe 106 relative to a field of view 202 which includes a pleura 204. As shown, the orientation 200 may be defined by three orthogonal planes including an azimuthal plane 210, an elevation plane 215, and a coronal plane. The azimuthal plane 210 captures image data from a sagittal view of the probe 106, and the elevation plane 215 captures image data from a transverse view of the probe 106. The coronal plane captures image data from a view parallel to the probe 106. For example, in a Cartesian coordinate system in which the Z-axis is defined as extending through a body, the coronal plane may be defined as an XY plane. According to the orientation 200, the azimuthal plane 210 and the elevation plane 215 are shown perpendicular to the pleura 204, while the coronal plane is parallel to the pleura 204. During a lung ultrasound, it may be desired to orient the probe 106 such that the ultrasound beam in the azimuthal plane 210 and the elevation plane 215 are perpendicular to the pleura 204, resulting in an image with optimal quality. In other words, for three-dimensional ultrasound imaging as is described herein, it may be desired to orient the probe 106 such that the coronal plane is parallel to the pleura 204.

Figure 5A:
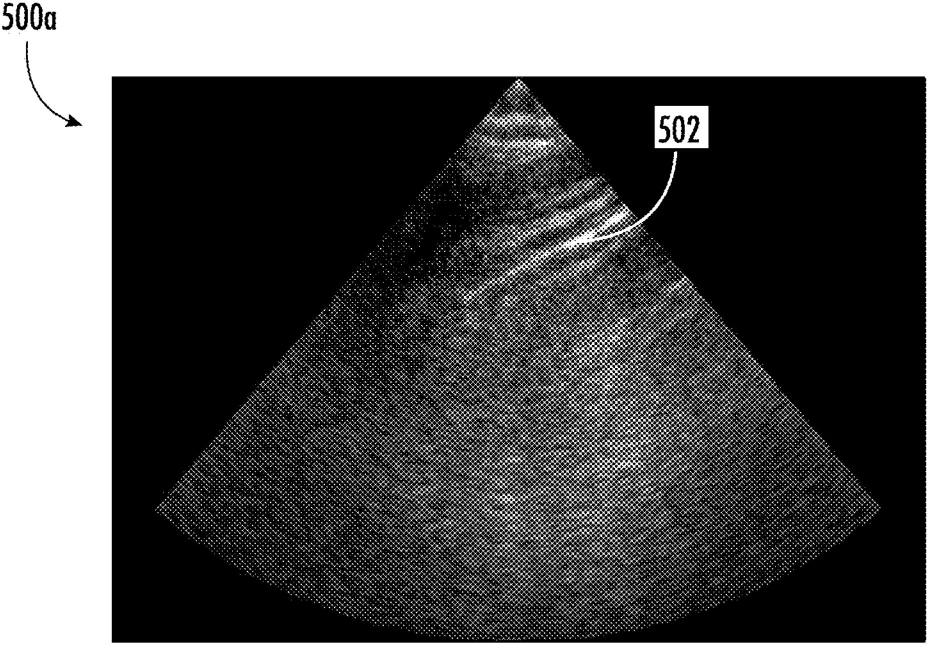
FIG. 5A is an illustration of an ultrasound image acquired using an ultrasound probe, according to an example embodiment.
Figure 5B:
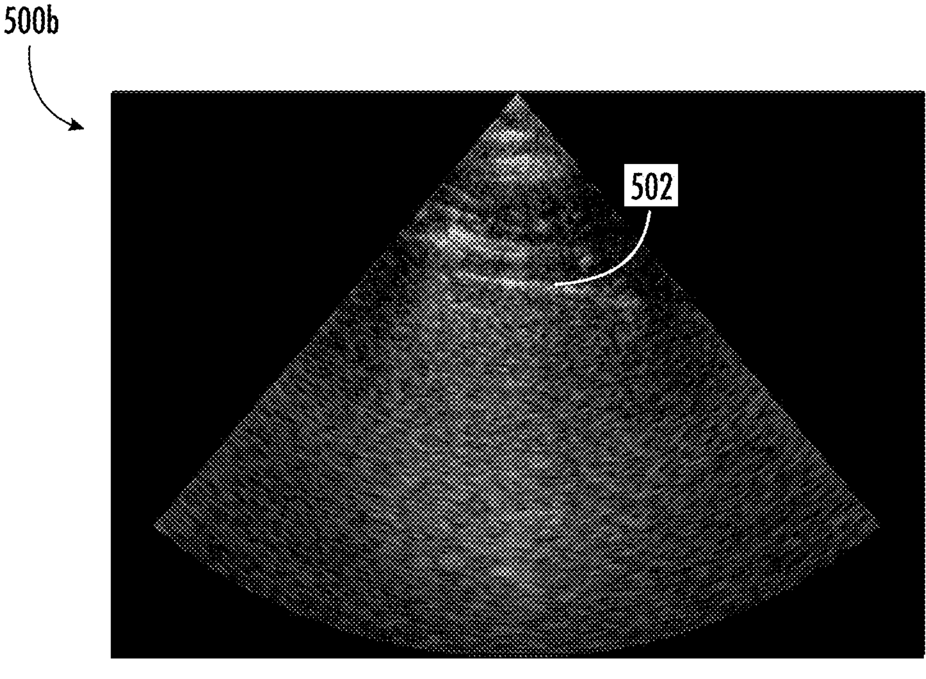
FIG. 5B is an illustration of another ultrasound image acquired using the ultrasound probe, according to an example embodiment.

When positioning the probe 106 on the patient, a position of the probe 106 is naturally perpendicular to the body of the patient. However, the pleura 204 may not be parallel to the body such that the pleura 204 is not perpendicular to the probe 106, as suggested by FIG. 2, but rather can be shifted at an angle (e.g., as represented in FIGS. 5A and 5B). When acoustic transmission is parallel to the probe 106, depending on the angle of the pleura 502, an image captured may have a degraded image quality, as described herein. Moreover, the positioning of the patient's pleura may be unique to an individual anatomy of the patient, meaning the position of a first patient's pleura may differ from a position of a second patient's pleura, and so on. This may be corrected by reorienting acoustic transmission of the probe 106, therefore adjusting the ultrasound signal transmitted to be as perpendicular to the pleura. This may also be corrected, by a user of the probe 106 reorienting the probe 106. Rather than relying on the expertise/skill of the sonographer to orient the probe 106 such that the pleura 502 is perpendicular to the ultrasound beam in the azimuthal plane 210 and the elevation plane 215, the transmit direction of the probe 106 may be automatically adjusted, as described herein, such that the probe 106 is configured to capture ultrasound images from a direction where the pleura is substantially perpendicular to the ultrasound beam.

When capturing data of a second anatomical feature that moves with respect of a first anatomical (e.g., as described herein, B-lines that move with respect to the pleura), it may be desired to determine a plane in which the first anatomical feature lies in. Continuing the example, with the pleura, the pleura may be parallel to the coronal plane, but in multiple cases, it can be shifted such that it is not parallel (e.g., the pleura may be substantially parallel or not parallel to the coronal plane). Determining the plane of the pleura may allow for a number of slices to be extract along a second plane that is parallel to the plane which may allow for an optimal view of the B-lines, as described below with reference to method 400 and FIGS. 7A-7D.

Figure 3:
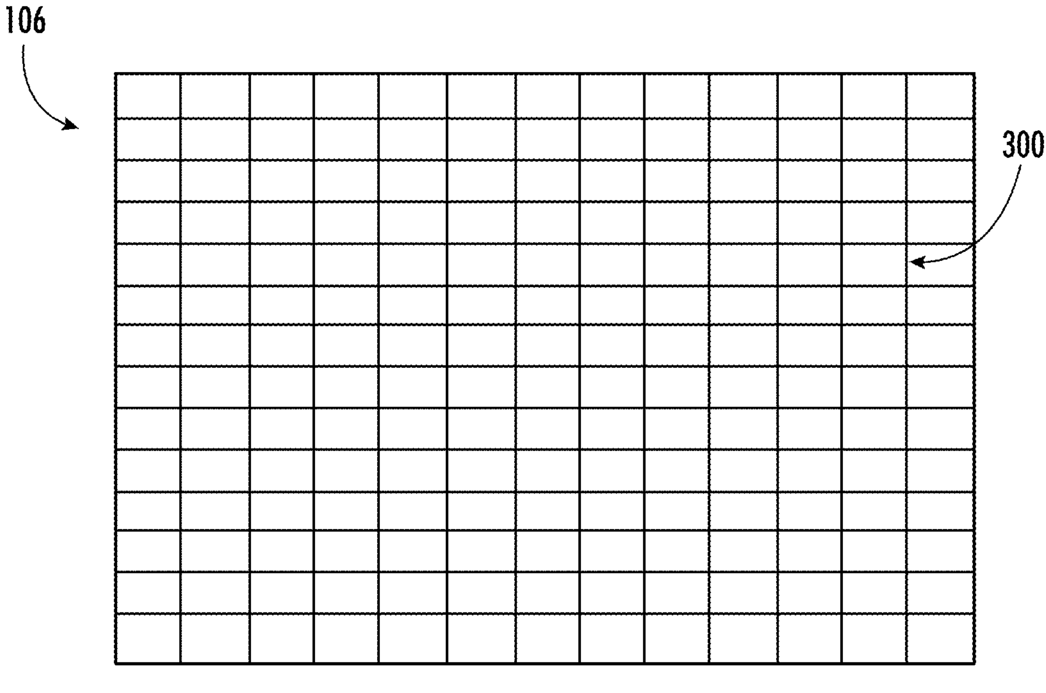
FIG. 3 is an illustration of a configuration of the ultrasound probe used in the ultrasound imaging system of FIG. 1, according to an example embodiment.

Referring to FIG. 3, a matrix configuration 300 of the ultrasound probe 106 is shown. The matrix configuration 300 refers to a configuration of the signal elements 108 within the ultrasound probe 106. More specifically, the matrix configuration 300 may include a 2D array of the signal elements 108 such that the probe 106 is configured to capture image data from several planes (e.g., a sagittal plane, a coronal plane, a transverse plane, etc.). In other words, with the matrix configuration 300, the probe 106 may obtain ultrasound images from a plurality of scanning planes. More specifically, as described herein, the probe 106 may be configured to obtain ultrasound images of a patient's lung from a sagittal plane, a coronal plane, and/or a transverse plane at a number of angles between an anatomical feature and the probe 106 and/or the ultrasound between. According to an example configuration of the probe 106, the matrix configuration 300 may include a 2D array of 6,000 elements (e.g., signal elements 108).

As described herein, with the matrix configuration 300, the orientation of the probe 106 may be adjusted with respect to the pleura (e.g., step 405 of method). In other words, although at an initial orientation of the probe 106, the azimuthal plane 210 and the elevation plane 215 show that the probe 106 and/or the ultrasound beam are not perpendicular to pleura, the matrix configuration 300 allows the probe 106 to be adjusted to capture image data in which the probe 106 and/or the ultrasound beam is perpendicular to the pleura based on the anatomy of the patient being imaged during the lung ultrasound. As described herein an orientation of the pleura, may aid in determining a second anatomical feature (e.g., B-lines) and it may be desirable for the orientation of the pleura to be substantially parallel to the coronal plane.

Figure 4:
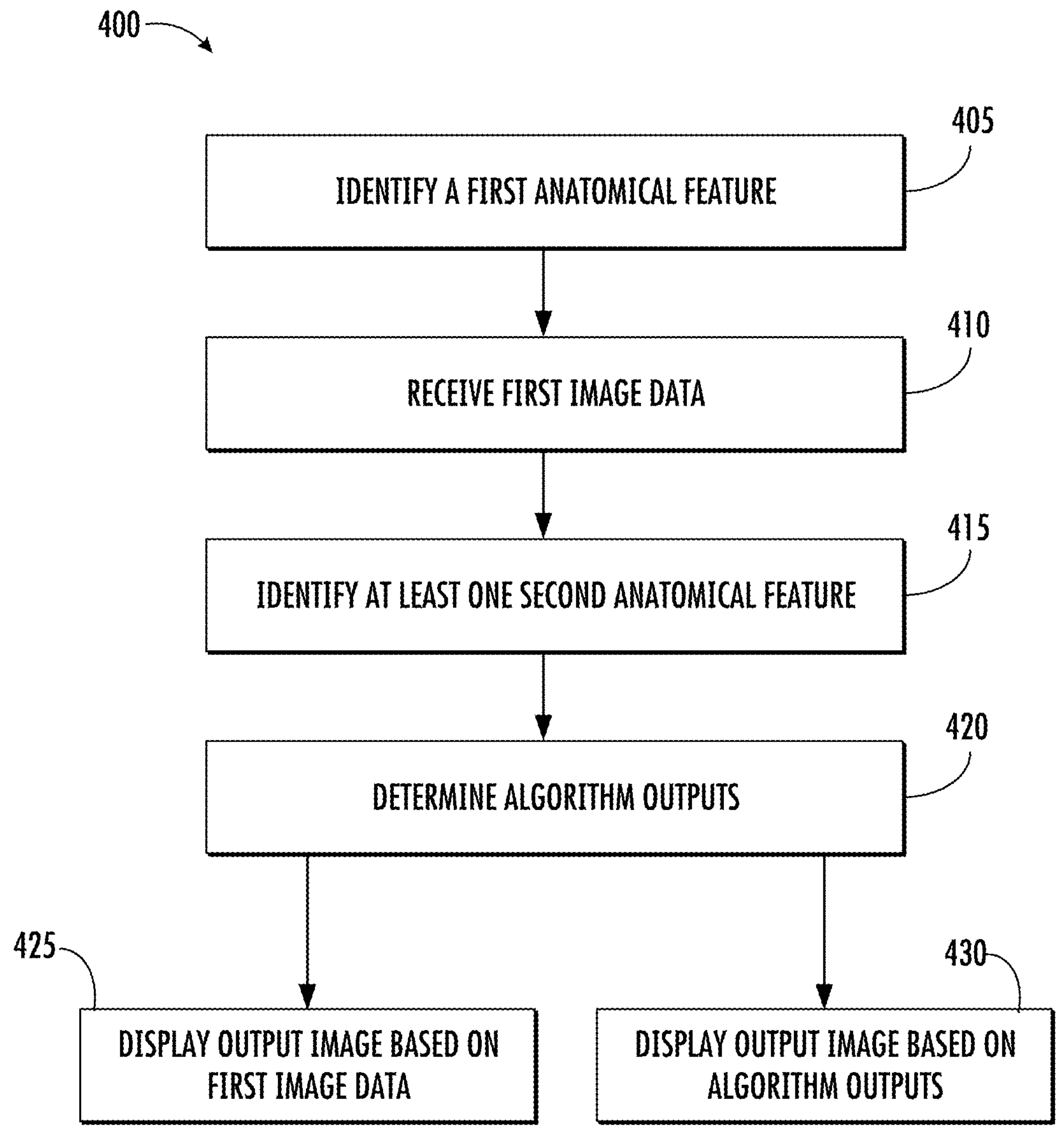
FIG. 4 is a flow chart illustrating a method for ultrasound imaging using the ultrasound imaging system of FIG. 1, according to an example embodiment.

Referring to FIG. 4, a flow chart illustrating a method 400 for three-dimensional ultrasound imaging using an ultrasound imaging system is shown. In at least one embodiment, the ultrasound imaging system referred to by method 400 is the ultrasound imaging system 100 described above with reference to FIG. 1, and method 400 may be implemented by the ultrasound imaging system 100. In some embodiments, method 400 may be implemented as executable instructions in a memory of the ultrasound imaging system 100, such as the memory 118 of FIG. 1.

As shown in FIG. 4, at step 405, method 400 includes identifying a first anatomical feature. As described herein, the transducer of the ultrasound imaging system 100 is configured to transmit and receive an ultrasound signal in a three dimensional volume. The three-dimensional volume includes a plurality of slices in a number of views (e.g., a transverse view, a coronal view, a sagittal view). At step 405, image data (e.g., a first image data, a second image data) may be sampled to identify the first anatomical feature in the image data. Processing of the ultrasound signals allows for image construction. Processing ultrasound signals may include converting the received echoes from the probe 106 into electrical signals, passing the electrical signals through the receive beamformer 112 for ultrasound data, and performing beamforming techniques to generate an image. Processing of the ultrasound signals occurs along second planes to receive the image data. The second planes may be planes perpendicular to the coronal plane. For example, the second planes may be the azimuthal plane 210, as depicted in FIG. 5A, and the elevation plane 215, as depicted in FIG. 5B. In various embodiments, the image processing circuit 120 applies processing techniques to the constructed image to further improve quality of the constructed images (e.g., contrast adjustment, brightness adjustment, noise reduction, etc.).

In some embodiments, step 405 may be performed by the processing circuit 114. For example, as described herein, the image data may be obtained during a lung ultrasound, and therefore the first anatomical feature may include a pleura of the patient being imaged. It should be appreciated, however, that although the ultrasound imaging system 100 cannot capture an image of the lung cavity due to the lung cavity being filled with air, an image of the lung cavity may be derived using surrounding anatomical structures/features (e.g., ribs, the pleura 502, etc.) depicted in the image data.

Figure 6A:
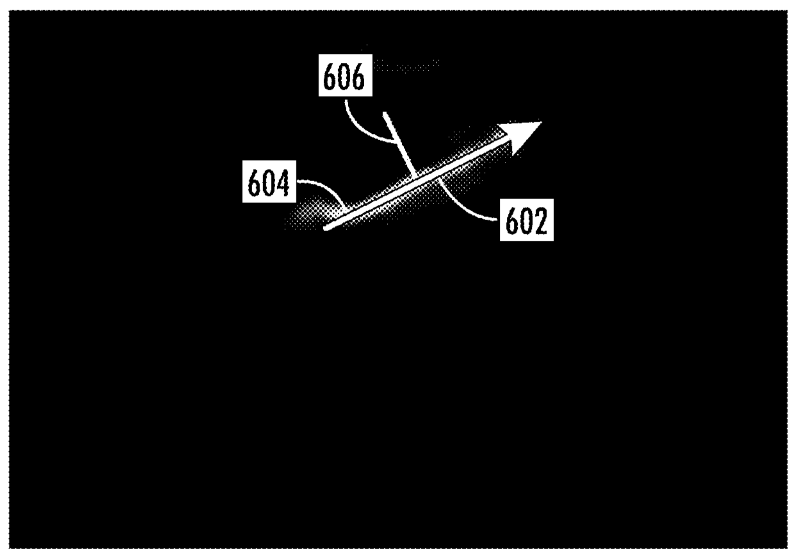
FIG. 6A is an illustration of the ultrasound image of FIG. 5A after processing, according to an example embodiment.
Figure 6B:
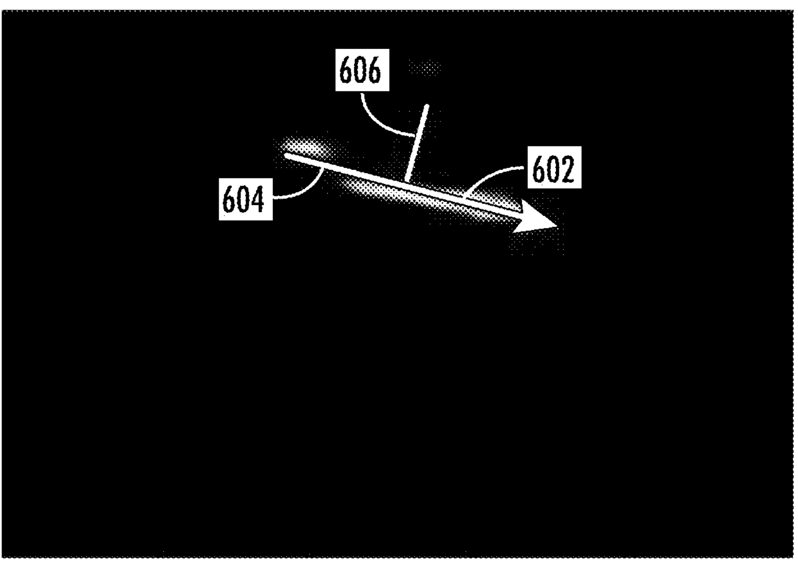
FIG. 6B is an illustration of the ultrasound image of FIG. 5B after processing, according to an example embodiment.
Figure 7A:
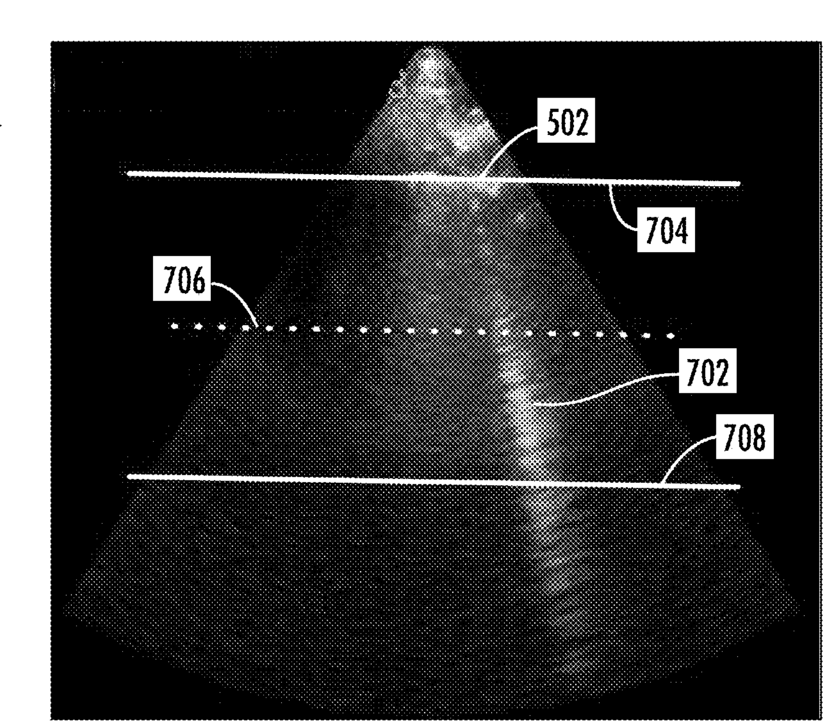
FIG. 7A is an illustration of another ultrasound image acquired from a three-dimensional volume using an ultrasound probe, according to an example embodiment.
Figure 7B:
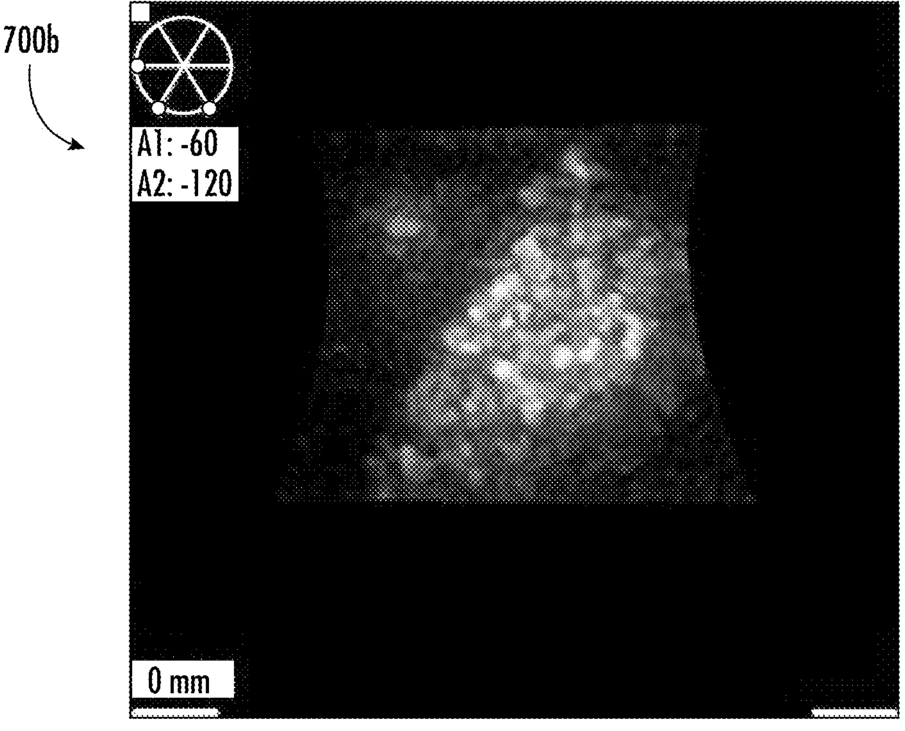
FIG. 7B is an illustration of another ultrasound image acquired from a first cross-sectional plane of the ultrasound image of FIG. 7A, according to an example embodiment.
Figure 7C:
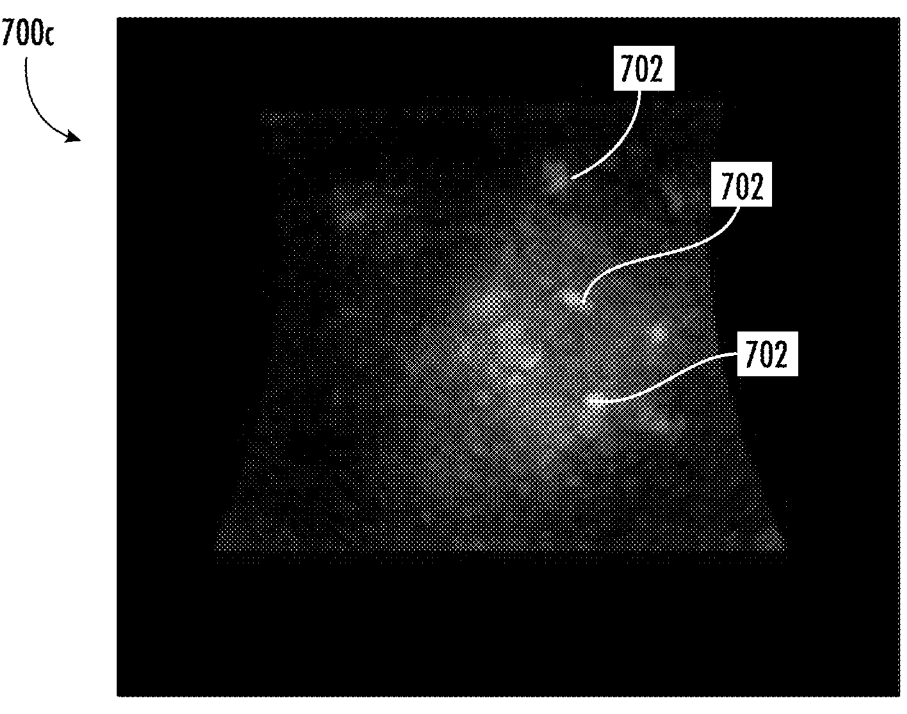
FIG. 7C is an illustration of another ultrasound image acquired from a second cross-sectional plane of the ultrasound image of FIG. 7A, according to an example embodiment.
Figure 7D:
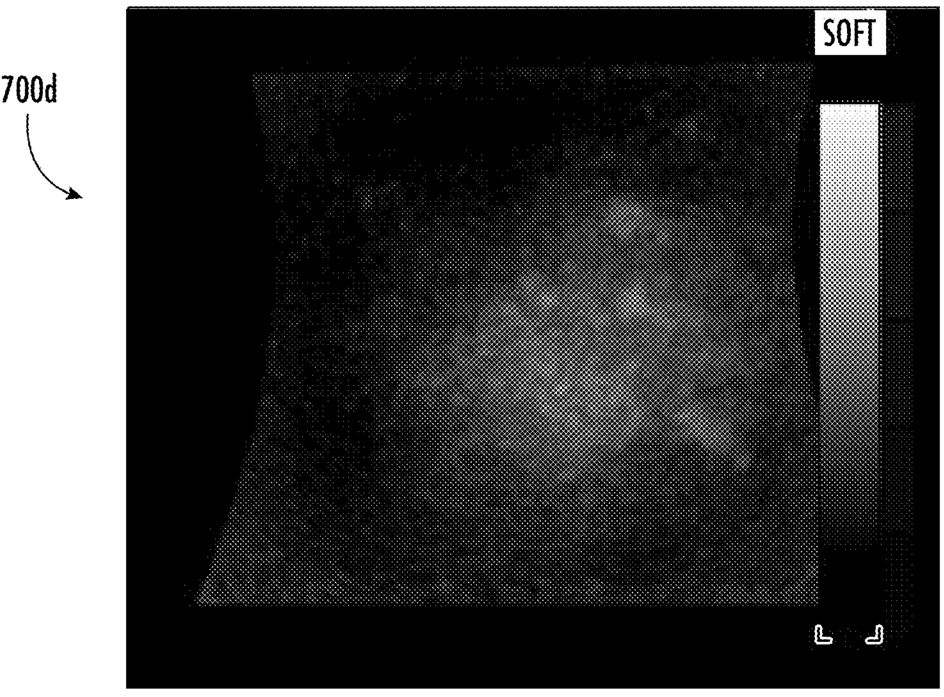
FIG. 7D is an illustration of another ultrasound image acquired from a third cross-sectional plane of the ultrasound image of FIG. 7A, according to an example embodiment.

Identifying the first anatomical feature at step 405 may include segmenting the first anatomical feature. Segmentation of the first anatomical feature can produce a binary mask of the first anatomical feature (e.g., FIGS. 6A and 6B depict a binary mask of the pleura). Although various methods can be employed to segment the first anatomical feature, one way to do so is by training a segmentation model (e.g., U-Net, Mask R-CNN, DeepLab, etc.). The trained model can analyze an image data taken along the second planes and output a probability for each data point (e.g., pixel) of the image data being the first anatomical feature or a background, i.e., not the first anatomical feature. Setting a threshold for the probabilities to determined which pixels classify as the first anatomical feature then creates the binary mask of the first anatomical feature for identification.

Segmentation of the first anatomical feature allows for a location and probe angle of the anatomical feature to be estimated. As described herein, by determining the location and probe angle of the first anatomical feature allows for a plane in which the first anatomical feature lies in to be determined. The determination of this plane allows for extraction of slices from the three-dimensional volume that are parallel to the plane, which can present information on a second anatomical feature. For example, with the pleura, because B-lines are at depths below the pleura and move with the pleura, extraction of slices parallel to a plane of the pleura can allow for detection of B-lines. As the pleura is substantially parallel to a patient's body, as described herein with reference to FIG. 2, in various embodiments, the plane and the extracted slices are substantially parallel to the coronal plane. This highlights the benefit of the use of three-dimensional ultrasound imaging for the detection of B-lines as the coronal view along with the sagittal view and the transverse view would be unattainable with two-dimensional ultrasound imaging.

A number of methods may be employed to fit the identified first anatomical feature into the plane. For example, Principal Component Analysis (PCA) or least square fitting can used. Fitting the identified first anatomical feature may provide a representation of the identified first anatomical feature The plane of the identified first anatomical feature forms vectors along the second planes of the image data (e.g., vector 604 as described with respect to FIGS. 6A and 6B) at a corresponding position of the plane.

Additionally, as described, determining an angle between the ultrasound beam and a normal of the first anatomical feature (i.e., the probe angle) may allow for determination of the plane. This may be done by first characterizing the identified first anatomical feature in a first image data and in a second image data as a first vector and a second vector, respectively, to determine the normal of the anatomical feature. The first image data and the second image data are taken along the second planes. A number of methods may be employed to fit the identified anatomical feature into a best-fit line. For example, orthogonal distance regression (ODR) can be used to calculate the best-fit line and determine the first vector and the second vector. ODR minimizes a sum of the squared orthogonal distances from each data point (e.g., the white pixels in the mask illustrated in FIGS. 6A and 6B) of the first anatomical feature to form a vector. Although the first vector and the second vector are shown in a 2D space, the first vector and the second vector may be expanded to the 3D space (e.g., by adding a zero in either an X or Y dimension, dependent on the plane).

The normal of the first anatomical feature may be determined by determining a vector that is perpendicular to both the first vector and the second vector. Cross product calculation of the first vector and the second vector can be used to determine the normal of the anatomical feature. With the normal of the anatomical feature determined, the angle between the ultrasound beam and the normal of the anatomical feature may be determined. The angle may be determined using trigonometric functions (e.g., arccosine). With the determination of the angle, the plane of the first anatomical feature may be determined that has the angle. In various embodiments, an optimal view of the first anatomical feature may be determined with the angle, and a second ultrasound signal that adjusts the first anatomical feature to the optimal view may be transmitted. For example, with a pleura, the optimal view may be such that the plane of the pleura is parallel to the coronal view and the angle is 0°.

As shown in FIG. 4, method 400 includes receiving first image data at step 410. As described with reference to step 405, the first image data is received from extracting slices from the three-dimensional volume that are parallel to the plane of the first anatomical feature. As described below with reference to FIGS. 11A and 11B, the first image data may be averaged to improve image quality. In bi-plane ultrasound imaging, which is typically used for ultrasound imaging of the lung, for example, the views shown are generally the sagittal view and the transverse view. The first image data may be taken along a view substantially parallel to the coronal view, which is perpendicular to the sagittal view and the transverse view. In other words, the first image data may be along cross-sectional planes of the sagittal view or transverse view.

As shown in FIG. 4, method 400 continues with identifying at least one second anatomical feature based on the first image data at step 415. The processing circuit 114 (e.g., the image processing circuit 120, the AI circuit 122, etc.) may be configured to identify the second anatomical feature using segmentation models (e.g., U-Net, Mask R-CNN, DeepLab). The identified second anatomical feature may be displayed as a binary mask. As described herein with reference to FIGS. 7C and 7D, among others, the second anatomical feature may be B-lines 702, in which the B-lines appear circular in the first image data.

As shown in FIG. 4, method 400 continues with determining algorithm outputs at step 420. The algorithm outputs include at least one of a number of second anatomical features identified, an area of at least one of the second anatomical features, or an area of at least one of the second anatomical features divided by an area of the first anatomical feature. Steps 420 may be determined by the processing circuit 114 based on the first image data. The number of second anatomical features may be determined from the segmented second anatomical features, as described with reference to step 415. An AI algorithm (e.g., along the processing circuit 114, the AI circuit 122, etc.) may match the segmented second anatomical features from the first image data by location to ensure that the second anatomical features are not being double counted. In other words, the second anatomical feature at a location in one of the first image data should remain in generally the same location in another of the first image data. As such, the number of second anatomical features is determined. The area of at least one of the second anatomical features may be determined with the segmentations of the anatomical feature. For example, the pixels from segmenting the second anatomical feature may be used to determine the area of at least one of the second anatomical features. Using a similar methodology of determining the area of the second anatomical feature, the area of the first anatomical feature may be determined. With this determination, the area of the second anatomical feature divided by the area of the first anatomical feature may be determined.

As shown in FIG. 4, method 400 includes displaying an output image based on the first image data at step 425 and/or the algorithm outputs at step 430. In some embodiments, the first image data and/or the algorithm outputs are displayed on the display device 132. The output image may include multiple ultrasound images of the first image data, such that an operator can visualize the second anatomical feature and other anatomical features. Additionally, displaying the algorithm outputs may provide the operator with more information on the second anatomical feature.

In various embodiments, method 400 also includes determining, for at least one first image data, a third plane that intersects the second anatomical feature in the first image data. The third plane may be perpendicular to a plane of the first image data. In various embodiments, the third plane may be parallel to the transverse plane or the sagittal plane. An operation of the ultrasound imaging system 100 may be used for viewing anatomical features (e.g., the first anatomical feature, the second anatomical feature, etc.) in the transverse view and/or sagittal view. By determining the third plane, a second image data along the third plane may be received, such that the second image data may be displayed. This may allow the operator to view the determined second anatomical feature in the transverse view and/or the sagittal view (i.e., a view the operator may be comfortable with). As described herein with reference to FIG. 11A, viewing the second anatomical feature in the transverse view or the sagittal view along with the coronal view may allow the operator to differentiate the second anatomical features from other anatomical features. For example, such as differentiating B-lines from Z-lines.

Referring to FIGS. 5A-5B, a bi-plane image of a first ultrasound image 500*a* acquired in a first plane and a second ultrasound image 500*b* acquired in a second plane is shown. The first plane is orthogonal to the second plane (e.g., an azimuth plane and an elevation plane). The first ultrasound image 500*a* and the second ultrasound image 500*b* may be acquired using techniques described in FIG. 4 (e.g., step 405). The first ultrasound image 500*a* and the second ultrasound image 500*b* show the pleura 502. A first image data and a second image data from the first ultrasound image 500*a* and the second ultrasound image 500*b*, respectively can be used to determine a location and probe angle of the pleura 502.

Referring to FIGS. 6A-6B, images of the first ultrasound image 500*a* and the second ultrasound image 500*b* after image processing (e.g., step 405) are shown. The pleura 502 in the first ultrasound image 500*a* and the second ultrasound image 500*b* are segmented, depicted by a segmented pleura 602. Segmentation of the pleura 502 may be performed using segmentation models disclosed herein. Data points (e.g., pixels) of the segmented pleura 602 are fit onto a line to create a vector 604. The vector 604 is used to determine a normal of the pleura 502 (e.g., by calculating a cross product of the vector 604 in both images to determine a normal vector, i.e., the normal of the pleura 502, perpendicular to both vectors 604). As disclosed herein (e.g., at step 405), the normal of the pleura 502 may be used to determine an angle between the normal of the pleura and the ultrasound beam, which allows for the determination of a plane that the pleura 502 lies in. In various embodiments, the plane is substantially parallel to the coronal plane. In various embodiments, a transmit direction to adjust a second ultrasound signal to a desired angle (e.g.,) 90° to receive a third image data set in which the pleura 502 is substantially parallel to the coronal plane is determined and a new three-dimensional volume is acquired.

Referring to FIGS. 7A-7D, a three-dimensional ultrasound image of a first ultrasound image 700*a*, a second ultrasound image 700*b*, a third ultrasound image 700*c*, and a fourth ultrasound image 700*d* is shown. The ultrasound images are extracted from a three-dimensional volume obtained from transmitting and receiving an ultrasound signal. The second ultrasound image 700*b*, the third ultrasound image 700*c*, and the fourth ultrasound image 700*d* are extracted (cross-sectional) slices that are parallel to the plane of the pleura 502 (e.g., substantially in the coronal view). Location of the slices are shown in the first ultrasound image 700*a* (e.g., slice 704 for the second ultrasound image 700*b*, slice 706 for the third ultrasound image 700*c*, and slice 708 for the fourth ultrasound image 700*d*). In the first ultrasound image 700*a*, a B-line 702 is visualized. Although the second ultrasound image 700*b* and the fourth ultrasound image 700*d* does not provide a clear detection of B-lines 702, the third ultrasound image show the B-lines 702 appearing as dots, showing three B-lines 702. In various embodiments, the B-lines 702 may not be visualized by a segmentation model in the third ultrasound image 700*c*, highlighting an importance of obtaining a plurality of slices.

Referring to FIGS. 8A-8D, a three-dimensional ultrasound image of a first ultrasound image 800*a*, a second ultrasound image 800*b*, a third ultrasound image 800*c*, and a fourth ultrasound image 800*d* is shown. The ultrasound images are extracted from a three-dimensional volume obtained from transmitting and receiving an ultrasound signal. The second ultrasound image 800*b*, the third ultrasound image 800*c*, and the fourth ultrasound image 800*d* are extracted (cross-sectional) slices that are parallel to the plane of the pleura 502. Location of the slices are shown in the first ultrasound image 800*a* (e.g., slice 804 for the second ultrasound image 800*b*, slice 806 for the third ultrasound image 800*c*, and slice 808 for the fourth ultrasound image 800*d*). In the first ultrasound image 800*a*, B-lines 702 appear faint and may not be properly detected. However, in the cross-sectional slices of the second ultrasound image 800*b*, the third ultrasound image 800*c*, and the fourth ultrasound image 800*d*, the B-lines 702 are properly detected and segmented by an algorithm. The B-line 702 in a first location 810 is detected as the same B-line 702 across the second ultrasound image 800*b*, the third ultrasound image 800*c*, and the fourth ultrasound image 800*d*. In various embodiments, and as described herein, coloring may be used to differentiate the B-lines 702. For example, a first B-line 702 may be highlighted as a first color in the slices that is different than a second color that a second B-line 702 is highlighted.

Referring to FIGS. 9A-9D, a three-dimensional ultrasound image of a first ultrasound image 900*a*, a second ultrasound image 900*b*, a third ultrasound image 900*c*, and a fourth ultrasound image 900*d* is shown. The ultrasound images are extracted from a three-dimensional volume obtained from transmitting and receiving an ultrasound signal. The second ultrasound image 900*b*, the third ultrasound image 900*c*, and the fourth ultrasound image 900*d* are extracted (cross-sectional) slices that are parallel to the plane of the pleura 502. Location of the slices are shown in the first ultrasound image 900*a* (e.g., slice 904 for the second ultrasound image 900*b*, slice 906 for the third ultrasound image 900*c*, and slice 908 for the fourth ultrasound image 900*d*). In the first ultrasound image 900*a*, B-lines 702 appear faint and may not be properly detected. However, in the cross-sectional slices of the second ultrasound image 900*b*, the third ultrasound image 900*c*, and the fourth ultrasound image 900*d*, the B-lines 702 are properly detected and segmented by an algorithm. Although the slices from FIG. 9 do not detect as many B-lines 702 as the slices from FIG. 8, extracting several slices may allow for a maximum number of B-lines 702 to be found.

Figure 10A:
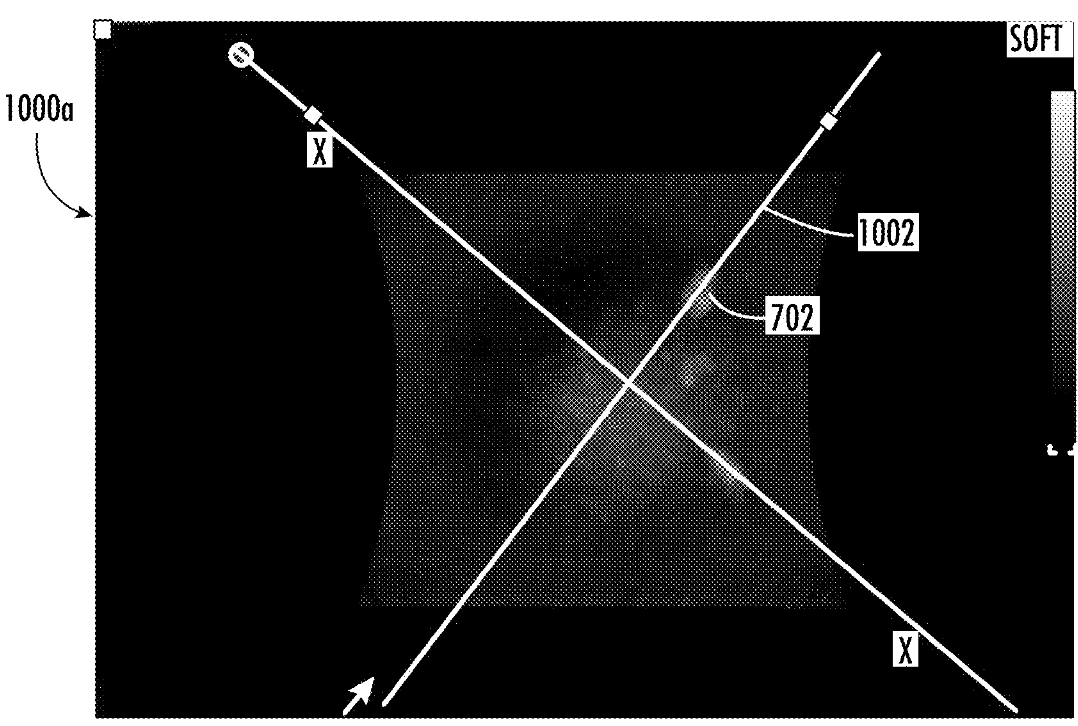
FIG. 10A is an illustration of another ultrasound image acquired from a three-dimensional volume, according to an example embodiment.
Figure 10B:
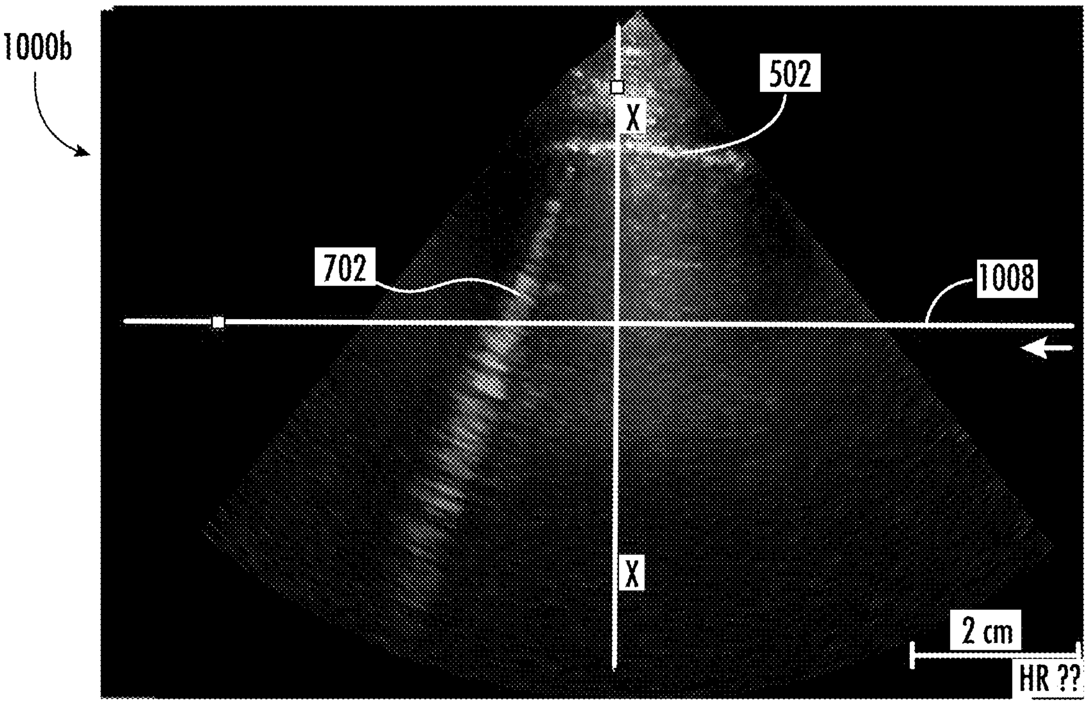
FIG. 10B is an illustration of another ultrasound image acquired from a first cross-sectional plane of the ultrasound image of FIG. 10A, according to an example embodiment.
Figure 10C:
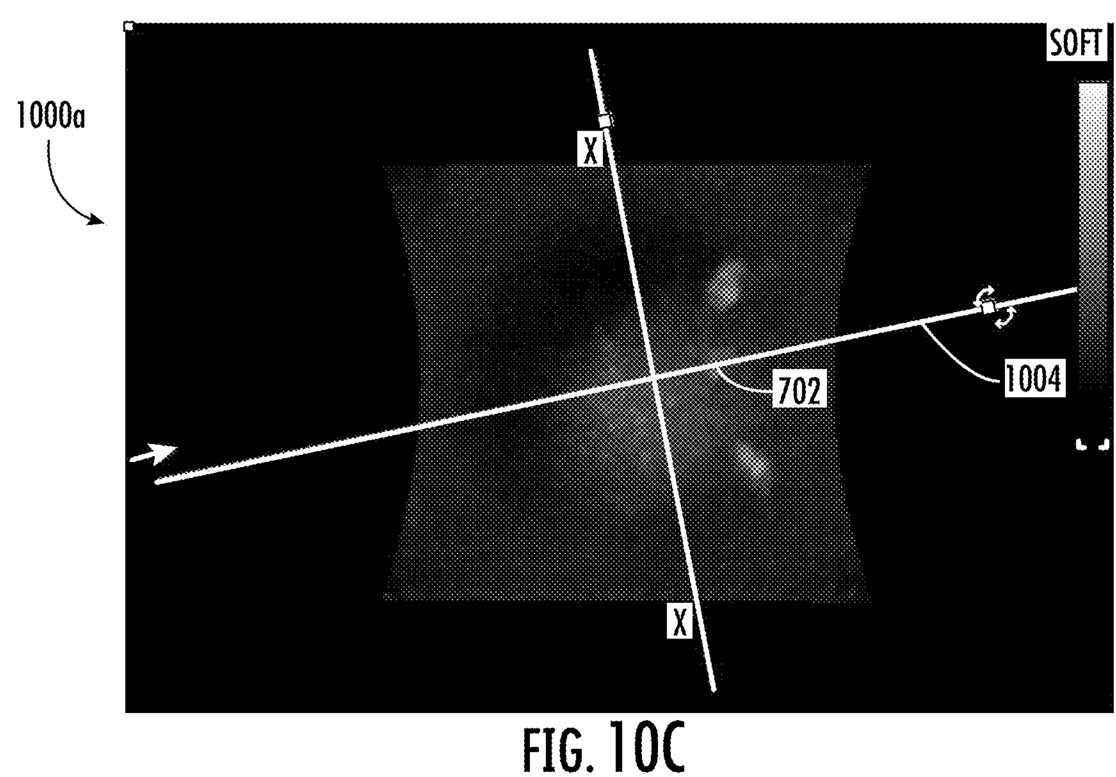
FIG. 10C is another illustration of the ultrasound image of FIG. 10A, according to an example embodiment.
Figure 10D:
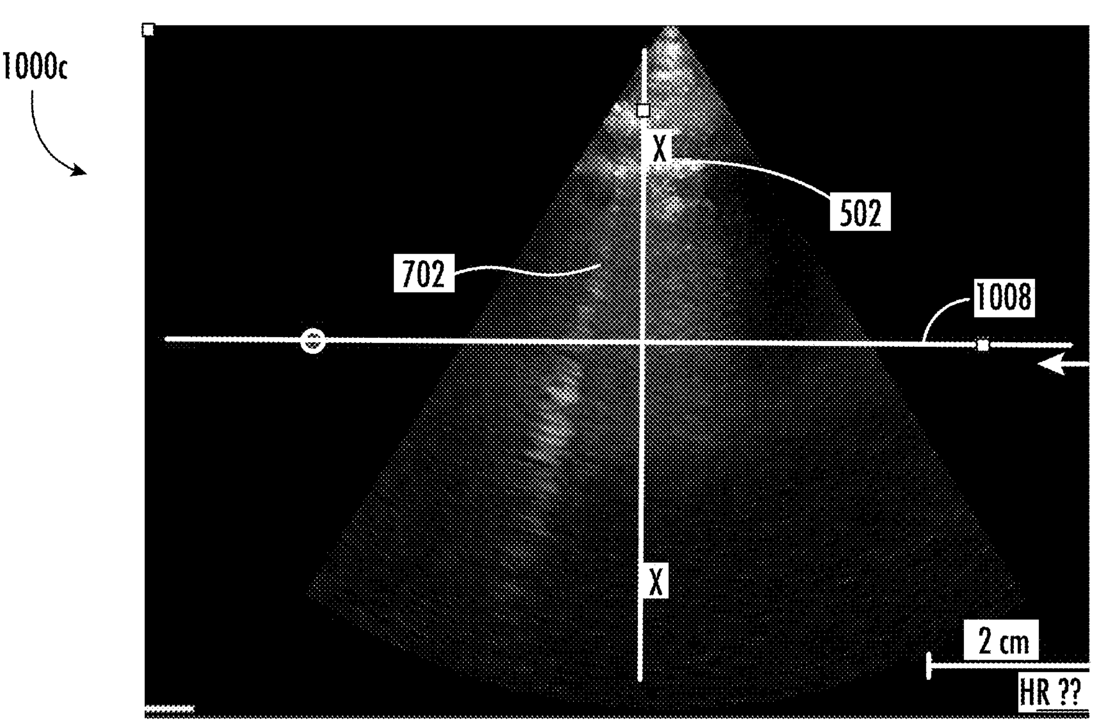
FIG. 10D is an illustration of another ultrasound image acquired from a first cross-sectional plane of the ultrasound image of FIG. 10C, according to an example embodiment.
Figure 10E:
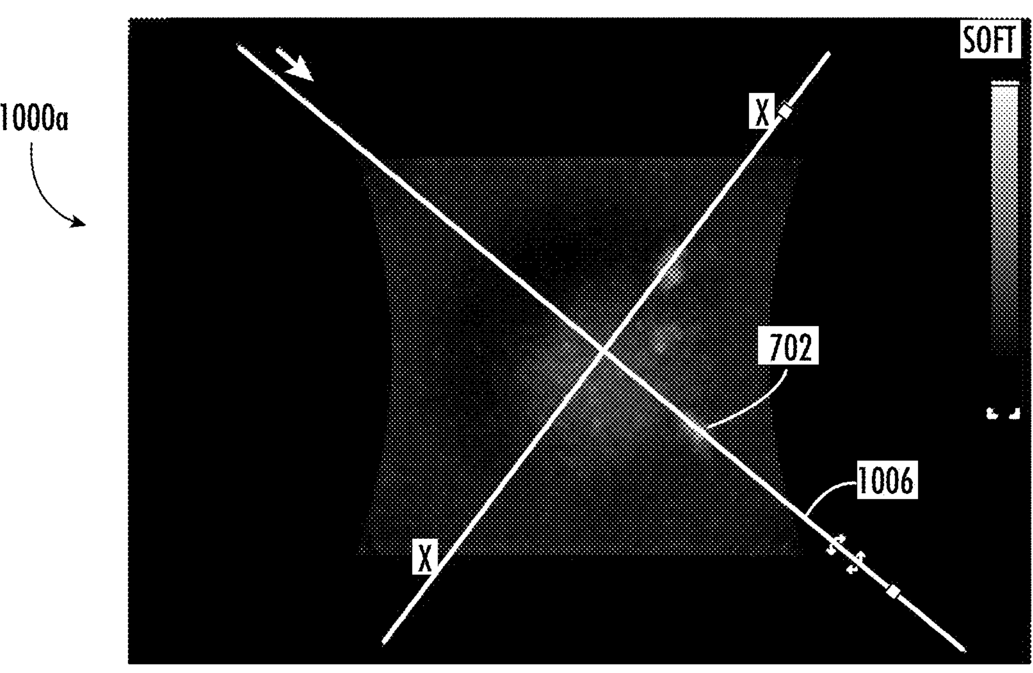
FIG. 10E is another illustration of the ultrasound image of FIG. 10A, according to an example embodiment.
Figure 10F:
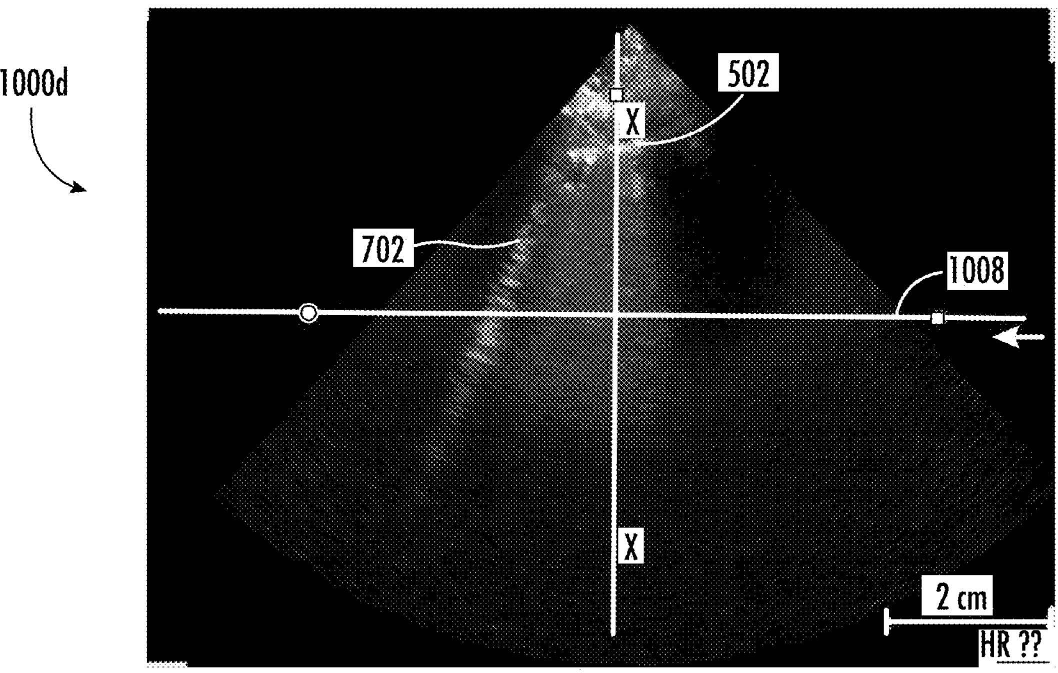
FIG. 10F is an illustration of another ultrasound image acquired from a first cross-sectional plane of the ultrasound image of FIG. 10E, according to an example embodiment.

Referring to FIGS. 10A-10F, a three dimensional ultrasound image of a first ultrasound image 1000*a*, a second ultrasound image 1000*b*, a third ultrasound image 1000*c*, and a fourth ultrasound image 1000*d* are shown. As described herein, the cross-sectional view shown in the first ultrasound image 1000*a* may not be a view that is preferred by an operator of the ultrasound imaging system 100. As such, ultrasound images in a preferred view (e.g., the transverse view, the sagittal view, the second ultrasound image 1000*b*, the third ultrasound image 1000*c*, the fourth ultrasound image 1000*d*, etc.) may be obtained (e.g., extracted from a 3D volume obtained from 3D ultrasound imaging). As shown in FIGS. 10A, 10C, and 10E, by determining a vector that intersects with the second anatomical feature (in this example, the B-lines 702), a plane corresponding to that vector may be determined by extending the vector into a view perpendicular to the cross-sectional view (e.g., the transverse view, the sagittal view, etc.). For example, as shown in FIG. 10A, vector 1002 intersects with the B-line 702 and FIG. 10B depicts the second ultrasound image 1000*b* taken along a plane of the vector 1002. In another example, FIG. 10C illustrates the same ultrasound image of FIG. 10A. However, in this example, a vector 1004 intersects with another B-line 702 and FIG. 10D depicts the third ultrasound image 1000*c* taken along a plane of the vector 1004. In another example, as shown in FIG. 10E, vector 1006 intersects with another B-line 702 and FIG. 10F depicts the fourth ultrasound image 1000*d* taken along a plane of the vector 1006. In these example, a plane of the first ultrasound image 1000*a* may be represented as vector 1008 (e.g., in the second ultrasound image 1000*b*, the third ultrasound image 1000*c*, and the fourth ultrasound image 1000*d*) and is perpendicular to the images demonstrating the cross-sectional view of the ultrasound images. In various embodiments, as described herein with reference to FIGS. 8A-8D, colors may be used to differentiate the B-lines 702. For example, the B-line 702 in FIG. 10A may be represented as a first color, and in the second ultrasound image 1000*b*, the B-line 702 may be represented as the first color.

Figure 11A:
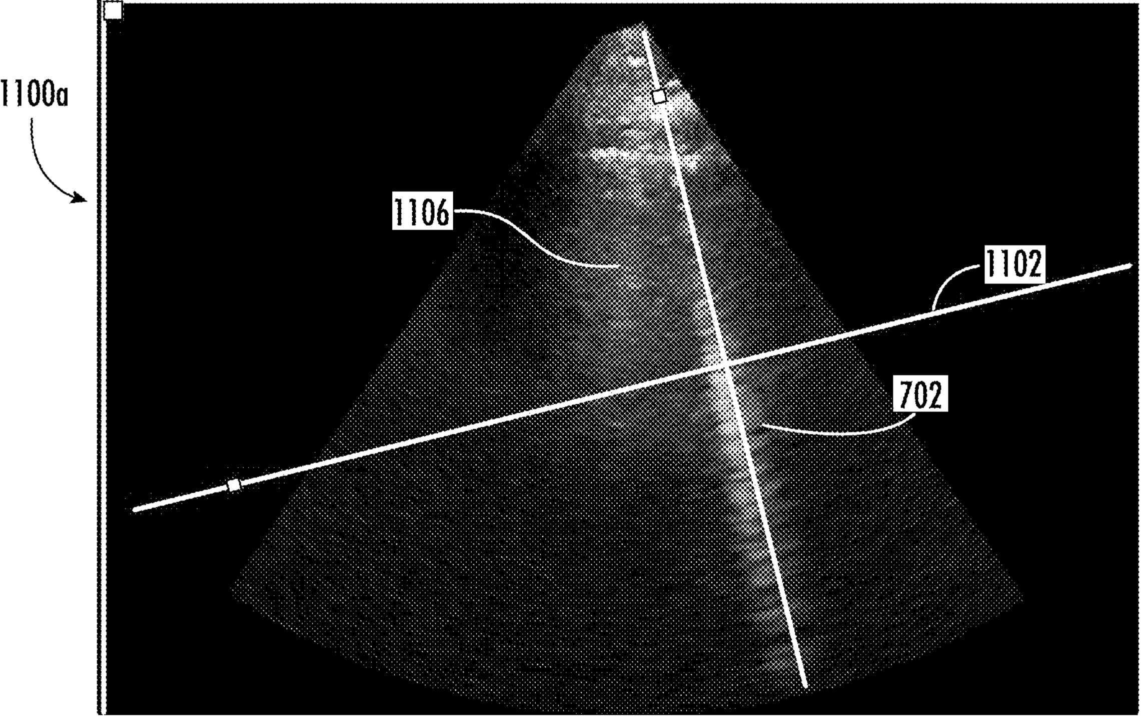
FIG. 11A is an illustration of another ultrasound image acquired from a three-dimensional volume, according to an example embodiment.
Figure 11B:
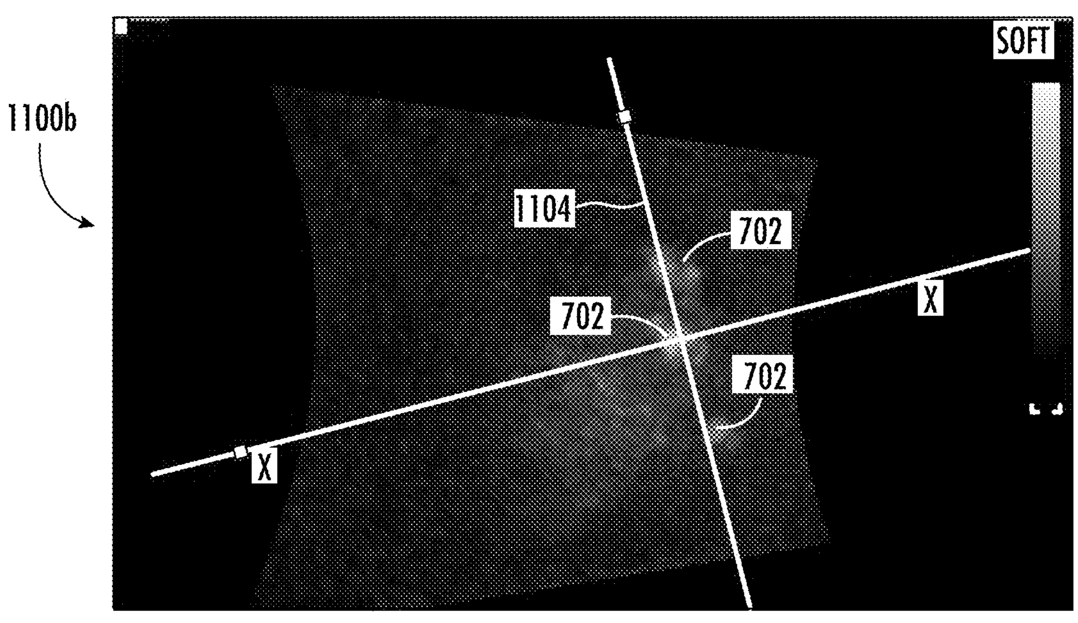
FIG. 11B is an illustration of another ultrasound image acquired from the three-dimensional volume, according to an example embodiment.
Figure 11C:
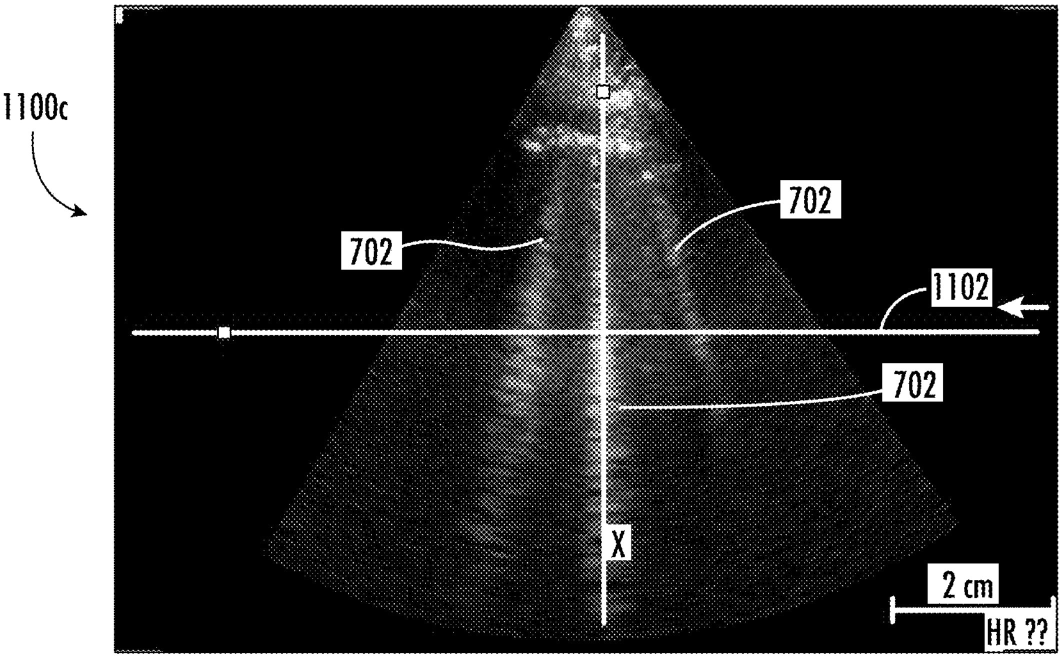
FIG. 11C is an illustration of another ultrasound image acquired from a cross-sectional plane of the ultrasound image of 11B, according to an example embodiment.

Additionally, by finding a vector that intersect with a maximum number of B-lines, a plane that the maximum number of B-lines appears on can be determined and displayed. Referring to FIGS. 11A-11C, a three dimensional ultrasound image of a first ultrasound image 1100*a*, a second ultrasound image 1100*b*, and a third ultrasound image 1100*c* are shown. The ultrasound images are extracted from a three-dimensional volume received from 3D ultrasound image data. When receiving an image in the transverse view and/or the sagittal view (e.g., first ultrasound image 1100*a*, first ultrasound image 1000*a*, first ultrasound image 800*a*, among others), the image may be used to differentiate B-lines from Z-lines. For example, the first ultrasound image 1100*a* shows a Z-line 1106 and a B-line 702. A cross-sectional (e.g., along the coronal view) image of the first ultrasound image 1100*a* may depict both the Z-line 1106 and the B-line 702 depending on where a slice for the cross-sectional image is extracted. However, by using the first ultrasound image 1100*a*, the Z-line 1106 may be differentiated from the B-line 702 based on a length of the lines in the first ultrasound image 1100*a* as the B-line 702 has a longer than the Z-line 1106.

The first ultrasound image 1100*a* may be used to extract a number of planes, including cross-sectional plane 1102. The second ultrasound image 1100*b* shows an image taken along the cross-sectional plane 1102. In the second ultrasound image 1100*b*, three B-lines 702 are detected. By determining a vector 1104 that intersects the three B-lines 702, the third ultrasound image 1100*c* can be extracted from a plane of the vector 1104. As such, an operator may view the third ultrasound image 1100*c* to know the maximum number of B-lines of a patient. As described herein, finding the plane that the maximum number of B-lines appears on provides a consistent way for an operator to evaluate a lung of a patient and may solve current problems with a lung score being dependent on an expertise level of the operator.

Figure 12A:
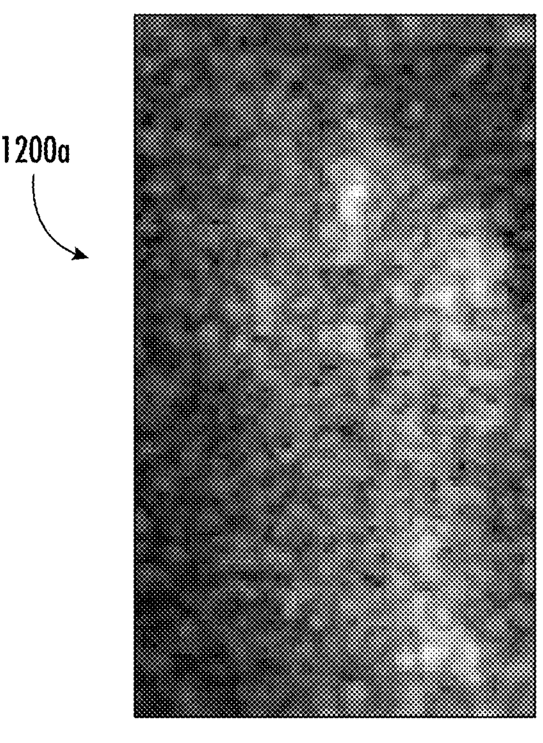
FIG. 12A is an illustration of a cross-sectional plane of an acquired ultrasound image showing anatomical features, according to an example embodiment.
Figure 12B:
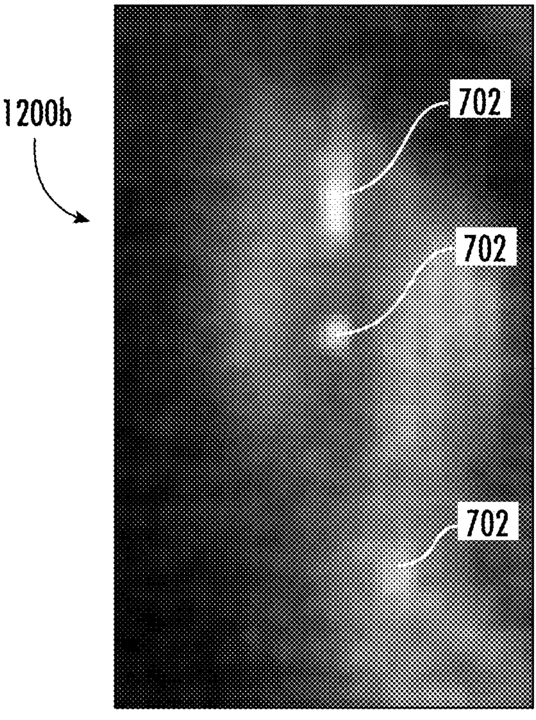
FIG. 12B is an illustration of averaged cross-sectional planes including the ultrasound image of FIG. 12A, according to an example embodiment.

Referring to FIGS. 12A and 12B, a first ultrasound image 1200*a* and a second ultrasound image 1200*b* are shown. The first ultrasound image 1200*a* is extracted from one cross-sectional plane while the second ultrasound image 1200*b* is an average of a plurality of cross-sectional planes. As shown, signal-to-noise ratio may be improved by averaging a plurality of cross-sectional planes rather than extracting only one for display and processing. Additionally, averaging cross-sectional planes may help in differentiating noise from B-lines in the cross-sectional view as B-lines move with the pleura and may appear more prominent in an ultrasound image where planes are averaged, as is depicted in the second ultrasound image 1200*b*.

The embodiments described herein have been described with reference to drawings. The drawings illustrate certain details of specific embodiments that provide the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As utilized herein, terms of degree such as "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that terms such as "exemplary," "example," and similar terms, as used herein to describe various embodiments, are intended to indicate that such embodiments are possible examples, representations, or illustrations of possible embodiments, and such terms are not intended to connote that such embodiments are necessarily extraordinary or superlative examples.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any element on its own or any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the drawings. It should be noted that the orientation of various elements may differ according to other exemplary embodiments, and that such variations are intended to be encompassed by the present disclosure.

As used herein, terms such as "engine" or "circuit" may include hardware and machine-readable media storing instructions thereon for configuring the hardware to execute the functions described herein. The engine or circuit may be embodied as one or more circuitry components including, but not limited to, processing circuitry, network interfaces, peripheral devices, input devices, output devices, sensors, etc. In some embodiments, the engine or circuit may take the form of one or more analog circuits, electronic circuits (e.g., integrated circuits (IC), discrete circuits, system on a chip (SOCs) circuits, etc.), telecommunication circuits, hybrid circuits, and any other type of circuit. In this regard, the engine or circuit may include any type of component for accomplishing or facilitating achievement of the operations described herein. For example, an engine or circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

An engine or circuit may be embodied as one or more processing circuits comprising one or more processors communicatively coupled to one or more memory or memory devices. In this regard, the one or more processors may execute instructions stored in the memory or may execute instructions otherwise accessible to the one or more processors. The one or more processors may be constructed in a manner sufficient to perform at least the operations described herein. In some embodiments, the one or more processors may be shared by multiple engines or circuits (e.g., engine A and engine B, or circuit A and circuit B, may comprise or otherwise share the same processor which, in some example embodiments, may execute instructions stored, or otherwise accessed, via different areas of memory).

Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be provided as one or more suitable processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given engine or circuit or components thereof may be disposed locally (e.g., as part of a local server, a local computing system, etc.) or remotely (e.g., as part of a remote server such as a cloud based server). To that end, engines or circuits as described herein may include components that are distributed across one or more locations.

An example system for providing the overall system or portions of the embodiments described herein might include one or more computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

Although the drawings may show and the description may describe a specific order and composition of method steps, the order of such steps may differ from what is depicted and described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described to explain the principals of the disclosure and its practical application to enable one skilled in the art to utilize the various embodiments and with various modifications as are suited to the particular use contemplated. Other substitutions, modifications, changes and omissions may be made in the design, operating conditions, and arrangement of the embodiments without departing from the scope of the present disclosure as expressed in the appended claims.

What is claimed is:

1. An ultrasound imaging system comprising:

a transducer configured to transmit and receive an ultrasound signal in a three-dimensional volume, the three-dimensional volume comprising a plurality of planes including a cross-sectional plane; and a processing circuit having a processor coupled to a memory device storing instructions thereon that, when executed, cause the processing circuit to perform operations comprising:

identifying a first anatomical feature based on initial image data obtained from the three-dimensional volume by an ultrasound probe along first planes intersecting a surface of the ultrasound probe, the first anatomical feature determined to be along the cross-sectional plane;

receiving first image data from the three-dimensional volume parallel to the cross-sectional plane;

identifying at least one second anatomical feature based on the first image data;

determining algorithm outputs based on the first image data, the algorithm outputs including at least one of a number of second anatomical features identified, an area of at least one of the second anatomical features, or an area of at least one of the second anatomical features divided by an area of the first anatomical feature; and displaying an output image based on at least one of the algorithm outputs or the first image data on a display screen of the ultrasound imaging system.

2. The ultrasound imaging system of claim 1, wherein the first planes include an azimuth plane and an elevation plane.

3. The ultrasound imaging system of claim 1, wherein the cross-sectional plane is determined from at least one of a location of the first anatomical feature or an angle between a transmit signal and a normal of the first anatomical feature.

4. The ultrasound imaging system of claim 1, wherein determining the cross-sectional plane comprises:

determining an angle between a transmit signal and a normal of the first anatomical feature;

determining a first transmit direction that would adjust the angle between the transmit signal and the normal of the first anatomical feature to a first angle that is substantially 0°; and automatically aligning a second ultrasound signal in the first transmit direction to adjust the angle to the first angle.

5. The ultrasound imaging system of claim 1, wherein the first image data includes more than one first image data averaged to create an averaged first image data, the averaged first image data used to identify the second anatomical feature.

6. The ultrasound imaging system of claim 1, wherein the first anatomical feature is a pleura and the second anatomical feature is a B-line, the first image data obtained at a depth below the pleura.

7. The ultrasound imaging system of claim 6, wherein the B-line appears to have a circular shape based on the first image data.

8. The ultrasound imaging system of claim 1, wherein the operations further comprises:

determining a third plane that intersects the second anatomical feature in the first image data, the third plane perpendicular to the cross-sectional plane;

receiving second image data along the third plane; and displaying the output image based on the second image data.

9. The ultrasound imaging system of claim 8, wherein one of the second anatomical features displayed based on the first image data is a first color, and the second anatomical feature displayed based on the second image data is the first color.

10. The ultrasound imaging system of claim 1, wherein the operations further comprise determining, based on the first image data, a third plane that includes a maximum number of second anatomical features, the third plane parallel to the cross-sectional plane.

11. The ultrasound imaging system of claim 10, wherein the operations further comprise determining a vector in the third plane that intersects the maximum number of second anatomical features, the vector extended to a fourth plane perpendicular to the cross-sectional plane.

12. The ultrasound imaging system of claim 11, wherein the operations further comprise receiving second image data along the third plane, receiving third image data along the fourth plane, and displaying the output image based on at least one of the second image data or the third image data.

13. An ultrasound imaging system comprising:

a transducer configured to transmit and receive an ultrasound signal in a three-dimensional volume, the three-dimensional volume comprising a plurality of planes including a cross-sectional plane;

an image processing circuit configured to identify a first anatomical feature based on initial image data obtained from the three-dimensional volume and receive first image data from the three-dimensional volume parallel to the cross-sectional plane; and a control circuit configured to:

determine algorithm outputs based on the first image data, the algorithm outputs including at least one of a number of second anatomical features identified, an area of at least one of the second anatomical features, or an area of at least one of the second anatomical features divided by an area of the first anatomical feature; and display an output image based on at least one of the algorithm outputs or the first image data on a display screen of the ultrasound imaging system.

14. The ultrasound imaging system of claim 13, wherein the second anatomical features are B-lines.

15. The ultrasound imaging system of claim 13, wherein the cross-sectional plane is determined by:

identifying at least one of the second anatomical features based on the initial image data obtained along first planes perpendicular to the cross-sectional plane; and determining a second plane that the at least one second anatomical feature is located, the cross-sectional plane parallel to the second plane.

16. The ultrasound imaging system of claim 13, wherein the control circuit is further configured to determine a second plane that intersects the at least one second anatomical feature in the first image data, the second plane perpendicular to the cross-sectional plane, and wherein second image data is received along the second plane.

17. The ultrasound imaging system of claim 13, wherein the control circuit is further configured to determine, based on the first image data, a second plane that intersects a maximum number of second anatomical features in the first image data, the second plane perpendicular to the cross-sectional plane.

18. A method comprising:

identifying, by a processing circuit, a first anatomical feature based on initial image data obtained from a three-dimensional volume by an ultrasound probe along first planes intersecting a surface of the ultrasound probe, the first anatomical feature determined to be along a cross-sectional plane;

receiving, by the processing circuit, first image data from the three-dimensional volume parallel to the cross-sectional plane;

identifying, by the processing circuit, at least one second anatomical feature based on the first image data;

determining, by the processing circuit based on the first image data, algorithm outputs including at least one of a number of second anatomical features identified, an area of at least one of the second anatomical features, or an area of at least one of the second anatomical features divided by an area of the first anatomical feature; and displaying an output image based on at least one of the algorithm outputs or the first image data on a display screen of an ultrasound imaging system.

19. The method of claim 18, further comprising determining, based on the first image data, a third plane that includes a maximum number of second anatomical features, the third plane perpendicular to the cross-sectional plane.

20. The method of claim 18, further comprising:

determining, based on the first image data, a third plane that intersects the second anatomical feature in the first image data, the third plane perpendicular to the cross-sectional plane;

receiving second image data along the third plane; and displaying the output image based on the second image data.

* * * * *